US008697349B2

(12) United States Patent
Hoshino et al.

(10) Patent No.: US 8,697,349 B2
(45) Date of Patent: Apr. 15, 2014

(54) METHOD OF PRODUCING SOLID-PHASE BODY HAVING IMMOBILIZED MICROOBJECT AND THE USE THEREOF

(75) Inventors: Fumihiko Hoshino, Ichinomiya (JP); Osamu Watanabe, Nagoya (JP); Taiji Ikawa, Aichi-gun (JP); Makoto Mouri, Seto (JP); Mamiko Narita, Nagoya (JP); Masahito Shiozawa, Nagoya (JP)

(73) Assignee: Kabushiki Kaisha Toyota Chuo Kenkyusho, Aichi-Gun (JP)

( * ) Notice: Subject to any disclaimer, the term of this patent is extended or adjusted under 35 U.S.C. 154(b) by 810 days.

(21) Appl. No.: 12/289,586

(22) Filed: Oct. 30, 2008

(65) Prior Publication Data

US 2009/0169771 A1 Jul. 2, 2009

(30) Foreign Application Priority Data

Nov. 1, 2007 (JP) ................................ 2007-284783

(51) Int. Cl.
*B05D 5/12* (2006.01)
*G01N 33/554* (2006.01)

(52) U.S. Cl.
USPC .............................................. 435/4; 427/595

(58) Field of Classification Search
None
See application file for complete search history.

(56) References Cited

U.S. PATENT DOCUMENTS

| 4,894,339 | A | 1/1990 | Hanazato et al. |
| 5,034,428 | A | 7/1991 | Hoffman et al. |
| 5,482,867 | A | 1/1996 | Barrett et al. |
| 5,679,524 | A | 10/1997 | Nikiforov et al. |
| 6,066,438 | A | 5/2000 | Nicolau et al. |
| 6,413,680 | B1 | 7/2002 | Watanabe et al. |
| 2002/0150825 | A1 | 10/2002 | Watanabe et al. |
| 2003/0186311 | A1* | 10/2003 | Henderson et al. ............... 435/6 |
| 2004/0053354 | A1 | 3/2004 | Ikawa et al. |
| 2004/0198637 | A1 | 10/2004 | Schultz et al. |
| 2008/0146459 | A1 | 6/2008 | Iwakura et al. |

FOREIGN PATENT DOCUMENTS

| JP | A-2-79975 | 3/1990 |
| JP | A-06-016699 | 1/1994 |
| JP | A-11-021293 | 1/1999 |
| JP | A-11-083857 | 3/1999 |
| JP | A-11-248533 | 9/1999 |
| JP | A-11-248621 | 9/1999 |
| JP | A-11-312335 | 11/1999 |
| JP | A-2003-329682 | 11/2003 |
| JP | A-2004-93996 | 3/2004 |
| JP | A-2004-251801 | 9/2004 |
| JP | A-2004-347317 | 12/2004 |
| JP | A-2006-511797 | 4/2006 |
| JP | A-2006-233004 | 9/2006 |
| JP | A-2006-321719 | 11/2006 |
| JP | A-2007-51998 | 3/2007 |
| WO | WO 98/06007 | 2/1998 |
| WO | WO 2005/075996 A1 | 8/2005 |

OTHER PUBLICATIONS

Ikawa et al., "Molecular Scale Imaging of F-Actin Assemblies Immobilized on a Photopolymer Surface," Phys. Rev. Lett., Jan. 2007, vol. 98, issue 1, pp. 018101-1 through 018101-4.*
English translation of Nakayama et al., JP-A-2-79975, published Mar. 20, 1990 (IDS submitted Dec. 29, 2008).*
Hoshino et al., "Control of Molecular Orientation of Proteins Using Two-Stage Photoimmobilization," Biochemistry and Molecular Biology, Dec. 11-15, 2007, pp. 1-4, with English translation.
Sundberg et al., "Spatially-Addressable Immobilization of Macromolecules on Solid Supports," J. Am. Chem. Soc., vol. 117, No. 49, 1995, pp. 12050-12057.
Schena et al., "Quantitative Monitoring of Gene Expression Patterns with a Complementary DNA Microarray," Science, vol. 270, Oct. 20, 1995, pp. 467-470.
Nov. 2, 2009 Office Action issued in U.S. Appl. No. 10/377,799.
Feb. 24, 2009 Office Action issued in U.S. Appl. No. 10/377,799.
Aug. 15, 2008 Office Action issued in U.S. Appl. No. 10/377,799.
Jan. 25, 2008 Office Action issued in U.S. Appl. No. 10/377,799.
Sep. 13, 2007 Office Action issued in U.S. Appl. No. 10/377,799.
Dec. 28, 2006 Office Action issued in U.S. Appl. No. 10/377,799.
Dec. 18, 2006 Office Action issued in U.S. Appl. No. 10/377,799.
May 2, 2006 Office Action issued in U.S. Appl. No. 10/377,799.
Oct. 4, 2005 Office Action issued in U.S. Appl. No. 10/377,799.
Jul. 6, 2010 Examiner's Answer in U.S. Appl. No. 10/377,799.
Jun. 17, 2011 Decision on Appeal in U.S. Appl. No. 10/377,799.
Co-pending U.S. Appl. No. 10/377,799.
Jun. 17, 2011 Decision on Appeal issued in U.S. Appl. No. 10/377,799.

* cited by examiner

*Primary Examiner* — Shafiqul Haq
*Assistant Examiner* — Galina Yakovleva
(74) *Attorney, Agent, or Firm* — Oliff PLC

(57) ABSTRACT

A method for immobilizing microobject to a solid-phase material is provided. The method comprises a step of preparing the solid-phase material having on its surface an intermediate agent that includes a first element that is capable of interacting with at least the above microobject, and a microobject immobilizing step of immobilizing the microobject to the solid-phase material in a state in which the interaction of the intermediate agent is exhibited.

23 Claims, 13 Drawing Sheets

(a)
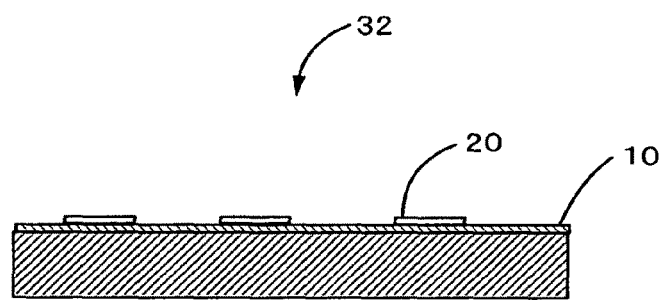
(b)
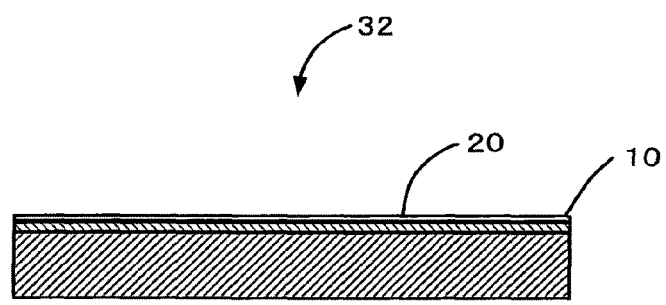
Fig.2

(a)
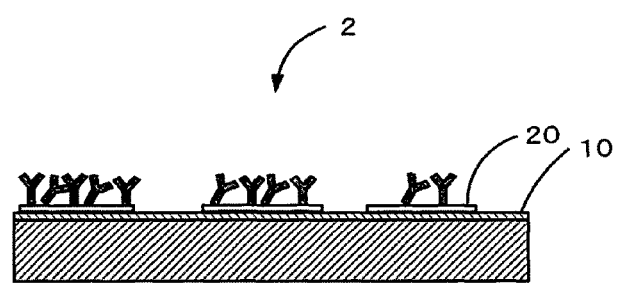
(b)
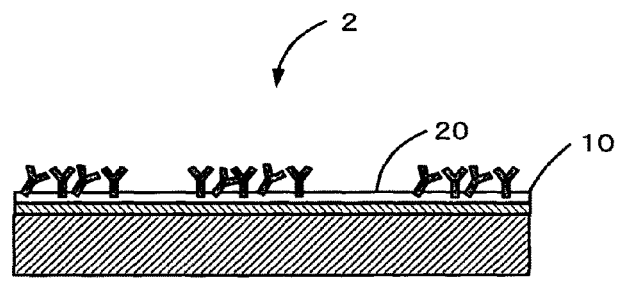
Fig.3

| Peptide No. position | Amino acid Sequence (abcdefg)₁(abcdefg)₂(abcdef)₃ | Peptide No. position | Amino acid Sequence (abcdefg)₁(abcdefg)₂(abcdef)₃ |
|---|---|---|---|
| 1 SEQ ID NO:46 | AIEEIAEAIEEIAKAIKKIA | 31 SEQ ID NO:76 | AIEKIAQAIEEIAHAIEKIA |
| 2 SEQ ID NO:47 | AIKKIAKAIKKIAKAIKKIA | 32 SEQ ID NO:77 | AIETIAQAIKKIAHAIETIA |
| 3 SEQ ID NO:48 | AITTKATAITTEATAITTIA | 33 SEQ ID NO:78 | AIELIAQAETTIAHAIELIA |
| 4 SEQ ID NO:49 | AILLKALGILLEALGILLIA | 34 SEQ ID NO:79 | AIKTIAQAELLIAHAIKTIA |
| 5 SEQ ID NO:50 | AIEKIAEAIEEIAKAIEKIA | 35 SEQ ID NO:80 | AIKLIAQAETLIAHAIKLIA |
| 6 SEQ ID NO:51 | AIETIAEAIKKIAKAIETIA | 36 SEQ ID NO:81 | AIEKIAIAIEEIAMAIEKIA |
| 7 SEQ ID NO:52 | AIELIAEAITTIAKAIELIA | 37 SEQ ID NO:82 | AIETIAIAIKKIAMAIETIA |
| 8 SEQ ID NO:53 | AIKEIAEAELLIAKAIKEIA | 38 SEQ ID NO:83 | AIELIAIAETTIGMAIKTIA |
| 9 SEQ ID NO:54 | AITLIAEAIKTIAKAITLIA | 39 SEQ ID NO:84 | AIKTIAIAELLIGMAIELIA |
| 10 SEQ ID NO:55 | AILEIAEAIKLIAKAILEIA | 40 SEQ ID NO:85 | AIKLIAIAETLIGMAIKLIA |
| 11 SEQ ID NO:56 | AITEIAEAILKIAKAITEIA | 41 SEQ ID NO:86 | AIEKIAFAIEEIASAIEKIA |
| 12 SEQ ID NO:57 | AILTIAEAITKIAKAILTIA | 42 SEQ ID NO:87 | AIETIAFAIKKIASAIETIA |
| 13 SEQ ID NO:58 | AIEKIATAIEEIALAIEKIA | 43 SEQ ID NO:88 | AIELIAFAETTIASAIKLIA |
| 14 SEQ ID NO:59 | AIETIATAIKKIALAIETIA | 44 SEQ ID NO:89 | AIKTIAFAELLIASAIETIA |
| 15 SEQ ID NO:60 | AIELIATAETTIALAIKEIA | 45 SEQ ID NO:90 | AIKLIAFAETLIASAIKLIA |
| 16 SEQ ID NO:61 | AIKEIATAELLIGLAIELIA | 46 SEQ ID NO:91 | AIEKIAWAIEEIAYAIEKIA |
| 17 SEQ ID NO:62 | AITLIATAIKTIALAETLIA | 47 SEQ ID NO:92 | AIETIAWAIKKIAYAIETIA |
| 18 SEQ ID NO:63 | AILEIATAIKLIALAELEIA | 48 SEQ ID NO:93 | AIELIAWAETTIAYAIKLIA |
| 19 SEQ ID NO:64 | AITEIATAILKIALAITEIA | 49 SEQ ID NO:94 | AIKTIAWAELLIAYAIETIA |
| 20 SEQ ID NO:65 | AILTEATAITKIALAELTIA | 50 SEQ ID NO:95 | AIKLIAWAETLIAYAIKLIA |
| 21 SEQ ID NO:66 | AIEKIAAAIEEIARAIEKIA | 51 SEQ ID NO:96 | AIEKIAVAIEEIAPAIEKIA |
| 22 SEQ ID NO:67 | AIETIAAAIKKIARAIETIA | 52 SEQ ID NO:97 | AIETIAVAIKKIAPAIETIA |
| 23 SEQ ID NO:68 | AIELIAAAETTIARAIELIA | 53 SEQ ID NO:98 | AIELIAVAETTIAPAIKLIA |
| 24 SEQ ID NO:69 | AIKTIAAAELLIARAIKTIA | 54 SEQ ID NO:99 | AIKTIAVAELLIAPAIETIA |
| 25 SEQ ID NO:70 | AIKLIAAAETLIARAIKLIA | 55 SEQ ID NO:100 | AIKLIAVAETLIAPAIKLIA |
| 26 SEQ ID NO:71 | AIEKIANAIEEIACAIEKIA | 56 SEQ ID NO:101 | KIEAIEKKIEAIEKKIEAIE |
| 27 SEQ ID NO:72 | AIETIANAIKKIACAIETIA | | |
| 28 SEQ ID NO:73 | AIELIANAETTIACAIKTIA | | |
| 29 SEQ ID NO:74 | AIKTIANAELLIACAIELIA | | |
| 30 SEQ ID NO:75 | AIKLIANAETLIACAIKLIA | | |

Fig.4

(a)
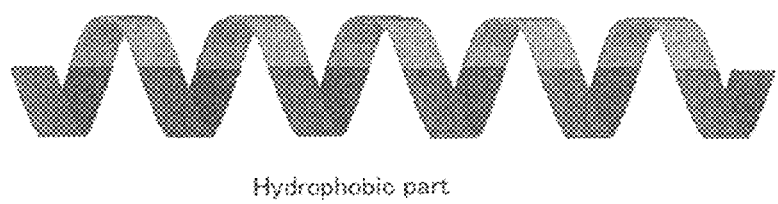
Hydrophobic part
(b)
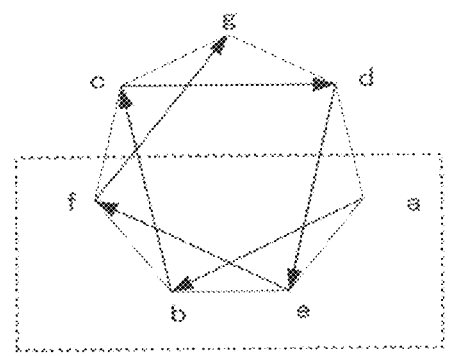
Hydrophobic part
Fig.5

|  | polymer coated | without polymer coated |
|---|---|---|
| Amount of fixed peptide | 7.53 | 3.53 |
| Amount of fixed antibody | 8.96 | 5.40 |
| orientation | 100 | 128 |

Fig.10

| IAT(I>G) | I A T A G A A G A A A G | SEQ ID NO:38 |
| --- | --- | --- |
| IAT(A5) | I A T A A A A A | SEQ ID NO:39 |
| IAT(A7) | I A T A A A A A A A | SEQ ID NO:40 |
| IAT(A9) | I A T A A A A A A A A A | SEQ ID NO:41 |
| IAT(G) | I A T G I A A I A A A I | SEQ ID NO:42 |
| IAT | I A T A I A A I A A A I | SEQ ID NO:43 |

Fig.11

|  | Sequence |  | Fixability | activity of antibody | Orientation |
|---|---|---|---|---|---|
| 1 | IAAAIAAIAAAI | SEQ ID NO:5 | 483 | 753 | 4.61 |
| 2 | VAAAIAAIAAAI | SEQ ID NO:6 | 388 | 612 | 4.67 |
| 3 | FAAAIAAIAAAI | SEQ ID NO:7 | 507 | 611 | 3.57 |
| 4 | PAAAIAAIAAAI | SEQ ID NO:8 | 353 | 435 | 3.64 |
| 5 | AAAAIAAIAAAI | SEQ ID NO:9 | 316 | 428 | 4.00 |
| 6 | LAAAIAAIAAAI | SEQ ID NO:10 | 432 | 481 | 3.29 |
| 7 | QAAAIAAIAAAI | SEQ ID NO:11 | 397 | 448 | 3.33 |
| 8 | IATAIAAIAAAI | SEQ ID NO:12 | 783 | 1362 | 5.14 |
| 9 | ATAAIAAIAAAI | SEQ ID NO:13 | 725 | 1113 | 4.54 |
| 10 | FATAIAAIAAAI | SEQ ID NO:14 | 725 | 991 | 4.04 |
| 11 | WATAIAAIAAAI | SEQ ID NO:15 | 848 | 1172 | 4.09 |
| 12 | VATAIAAIAAAI | SEQ ID NO:16 | 406 | 558 | 4.06 |
| 13 | LATAIAAIAAAI | SEQ ID NO:17 | 392 | 498 | 3.76 |
| 14 | AATAIAAIAAAI | SEQ ID NO:18 | 549 | 634 | 3.42 |
| 15 | PATAIAAIAAAI | SEQ ID NO:19 | 416 | 513 | 3.64 |
| 16 | TATAIAAIAAAI | SEQ ID NO:20 | 432 | 413 | 2.83 |
| 17 | IHTAIAAIAAAI | SEQ ID NO:21 | 805 | 1050 | 3.85 |
| 18 | IPTAIAAIAAAI | SEQ ID NO:22 | 1423 | 1777 | 3.69 |
| 19 | IITAIAAIAAAI | SEQ ID NO:23 | 729 | 782 | 3.17 |
| 20 | IMTAIAAIAAAI | SEQ ID NO:24 | 1295 | 1741 | 3.97 |
| 21 | ISTAIAAIAAAI | SEQ ID NO:25 | 1017 | 1573 | 4.57 |
| 22 | ITTAIAAIAAAI | SEQ ID NO:26 | 1020 | 1869 | 5.42 |
| 23 | IQTAIAAIAAAI | SEQ ID NO:27 | 1587 | 1893 | 3.52 |
| 24 | IASAIAAIAAAI | SEQ ID NO:28 | 786 | 1493 | 5.61 |
| 25 | IGSAIAAIAAAI | SEQ ID NO:29 | 982 | 1082 | 3.26 |
| 26 | IVSAIAAIAAAI | SEQ ID NO:30 | 885 | 1302 | 4.35 |
| 27 | ISSAIAAIAAAI | SEQ ID NO:31 | 730 | 1126 | 4.56 |
| 28 | ITSAIAAIAAAI | SEQ ID NO:32 | 878 | 1915 | 6.45 |
| 29 | IQSAIAAIAAAI | SEQ ID NO:33 | 2625 | 3107 | 3.50 |
| 30 | INSAIAAIAAAI | SEQ ID NO:34 | 1719 | 2248 | 3.86 |
| 31 | IAYAIAAIAAAI | SEQ ID NO:35 | 618 | 764 | 3.65 |
| 32 | IAEAIAAIAAAI | SEQ ID NO:36 | 889 | 1228 | 4.08 |
| 33 | IAIAIAAIAAAI | SEQ ID NO:37 | 417 | 717 | 5.08 |
| C1* | without peptide |  | 25 | 20 | 2.33 |
| C2* | anti-goat IgG dried and photo-fixed |  | 459 | 155 | 1.00 |
| C3* | EATAIAAIAAAI | SEQ ID NO:44 | 83 | 63 | 2.22 |
| C4* | EAAAIAAIAAAI | SEQ ID NO:45 | 118 | 58 | 1.44 |

*: C1 represents Comparative example 1

METHOD OF PRODUCING SOLID-PHASE BODY HAVING IMMOBILIZED MICROOBJECT AND THE USE THEREOF

CROSS-REFERENCE TO RELATED APPLICATION

This application claims priority to Japanese Patent Application No. 2007-284783, filed on Nov. 1, 2007, the contents of which are hereby incorporated by reference into the present application.

BACKGROUND OF THE INVENTION

1. Field of the Invention

The present invention relates to a technique of immobilizing microobject to a solid-phase material; more specifically, the present invention relates to a method of immobilizing a microobject via an intermediate agent and the use thereof.

2. Description of the Related Art

Application of materials produced by immobilizing microobjects such as proteins in solid-phase materials to diagnostic uses, analytical applications, reactor applications, sensor applications, etc has been sought for. Under such applications, unless proteins and the like have their sites such as catalytic sites immobilized in exposed states, their substantial interaction efficiencies to function are decreased. Thus, attempts are made to impart a constant directionality to microobjects such as proteins, to orient and immobilize the microobjects to the surfaces of solid-phase materials.

For example, one of well-known method of a technique of fixing orientation using physical adsorption involves introducing a plurality of amino-acids including a carboxyl group, by gene recombination, into the C-terminal side of a protein, i.e. a microobject, while orienting and fixing the protein to the surface of a solid-phase material by treatment with polylysine or the like (Japanese Patent Application Publication No. 2004-347317, hereinafter referred to as Patent Document 1). In addition, a method that entails introducing a hydrophobic polypeptide into an N-terminus or a C terminus by gene recombination and immobilizing such a protein to the surface of a substrate is known (Japanese Patent Application Publication No. 1990-79975, hereinafter referred to as Patent Document 2). Additionally, as a method of using a chemical bond to the surface of a solid-phase material is known; such method involves introducing an unnatural amino acid into a protein, i.e. an microobject, and then incorporating a reactive group that reacts with this unnatural amino acid into a solid-phase material, thus orienting and immobilizing the protein (Published Japanese Translations of PCT International Patent Application Publication No. 2006-511797, hereinafter referred to as Patent Document 3).

On the other hand, the present inventors have already developed a photo-immobilization method of immobilizing a microobject to a solid-phase material without using physical adsorption or chemical bonding (Japanese Patent Application Publication No. 2003-329682, hereinafter referred to as Patent Document 4). The photo-immobilization method distributes a microobject such as a protein onto the surface of a solid-phase material that contains a photoresponsive component which is capable of being deformed by light; the method deforms the vicinity of the surface of the solid-phase material around the microobject by light irradiation to thereby immobilize the microobject (i.e. light fixation).

BRIEF SUMMARY OF THE INVENTION

In any of the methods disclosed in the above Patent Documents, a part of an immobilization element such as a functional group or a compound for immobilizing a microobject is included in the solid-phase material. In addition, even in any of the methods disclosed in the above Patent Documents, direct interaction of the microobject with the solid-phase material is required for immobilizing the microobject to the solid-phase material, whereby the direct contact of the microobject with the solid-phase material is unavoidable. Therefore, the microobject is pervious to being affected by the solid-phase material and elements contained therein for immobilization as well as immobilization interaction. Additionally, degradation in the activity, the environmental durability, the storage stability, and the like might be caused in the case where the microobject is a biomolecule such as a protein. In particular, in the case with the oriented immobilization by physical adsorption and chemical bonding, a strong interaction between the solid-phase material and the microobject is necessary, and therefore the microobject might be adversely affected due to the immobilization element and the interaction therewith.

Moreover, as shown in Patent Document 1 to 3 above, an approach of gene recombination or the like is reasonably used to introduce a specific amino acid into a part of a microobject in order to orient and immobilize the microobject. However, many technical objects such as the obtainment of a protein to be immobilized, the establishment of gene introduction operation, the activation of the resulting protein and the like should be achieved to obtain a modified protein in which an original function is secured.

Thus, under the situation as to today, an attempt to avoid or restrain a direct interaction between the microobject and the solid-phase material to orient the microobject to the solid-phase material is limited merely to special cases.

In view of the aforestated subjects, one object of the present teachings disclosed herein is to provide a method to avoid or restrain a direct interaction between a microobject and a solid-phase material and orient and immobilize the microobject to the solid-phase material, and to make use of such method. In addition, another object of the present teachings is to provide a method of immobilizing a microobject without introduction of a special element for achieving the orientation and the like of the microobject into the microobject and to make use of such method. Additionally, another object of the present teachings is to provide an intermediate agent suitable for immobilizing a microobject to a solid-phase material.

The present inventors have found that microobject can be immobilized onto the solid-phase material by employing the immobilization principle that resides between the solid-phase material and the microobject while arranging an intermediate agent having an element that interacts with the microobject on the surface of a solid-phase material, under a state in which an interaction for orienting the microobject is caused between the intermediate agent and the microobject. Moreover, the inventors have further obtained a finding that the microobject is immobilized in a state in which the microobject is oriented to the solid-phase material due to the interaction between the microobject and the intermediate material. The present inventors have achieved the present teachings on the basis of these findings. The following means are provided according to the present teachings.

According to the present teachings, a method of producing a solid-phase body in which a microobject is immobilized to the solid-phase material is provided with a step of preparing the solid-phase material comprising on its surface an intermediate agent that includes a first element that is capable of interacting with at least the above microobject, and a microobject immobilizing step of immobilizing the microobject to the solid-phase material in a state in which the interaction of the intermediate agent is exhibited. In the present invention, the microobject preferably includes a polypeptide chain. More preferably, the microobject may be an antibody. The first element may also be capable of interacting with the solid-phase material.

In the method according to the present invention, the solid-phase material may be a photoresponsive material that contains a photoresponsive component that is capable of being deformed by light irradiation. Further, in the microobject immobilizing step, the microobjects may be immobilized to the solid-phase material by light irradiation in a state in which the microobjects are distributed on or in the vicinity of the surface of the solid-phase material. In addition, prior to the microobject immobilization step, an intermediate agent immobilization step of immobilizing the intermediate agent to the surface of the solid-phase material may be performed. In this case also, the solid-phase material may be of a photoresponsive material that contains a photoresponsive component that is capable of being deformed by light irradiation. Consequently in the intermediate agent immobilization step, the intermediate agents may be immobilized to the solid-phase material by light irradiation in a state in which the intermediate agents are distributed on or in the vicinity of the surface of the solid-phase material.

Moreover, the first element of the intermediate agent may be an element of capable of exhibiting a noncovalent interaction. The noncovalent interaction may be an electrostatic interaction or a hydrophilic interaction. Furthermore, the intermediate agent preferably has a sufficiently small molecular weight as compared with the molecular weight of the microobject The term 'sufficiently small as compared with the molecular weight of the microobject' in this specification refers to the molecular weight of the intermediate agent being within the range in which the effect by the intermediate agent and the fixability of the microobject by the solid-phase material are maintained. In addition, the intermediate agent is preferably prepared on the surface of the solid-phase material that has a layer thickness sufficiently small as compared with the total length of the microobject. The term 'sufficiently small as compared with the total length of the microobject' in this specification refers to the layer thickness of the intermediate being within the range in which the effect by the intermediate agent and the fixability of the microobject by the solid-phase material are maintained.

Additionally, the intermediate agent may further include a second element that is capable of interacting with the solid-phase material. The interaction of the second element may be a hydrophobic interaction.

Moreover, the intermediate agent may include a polypeptide chain. The polypeptide chain preferably has an α-helix structure; and more preferably in the α-helix structure, hydrophobic amino acid residues are predominantly arranged at least on one side. Furthermore, the α-helix structure may contain 50% or more of the hydrophobic amino acid residue. The α-helix structure may comprise an amino acid sequence in which 8 or more of the hydrophobic amino acid residues are consecutively arranged. The hydrophobic amino acid residue may be selected from alanine and isoleucine, and the polypeptide chain may have an α-helix structure that includes amino acid sequences selected from the table shown below. Furthermore, the intermediate agent preferably has an α-helix structure that is of a polypeptide chain having 12 to 20 amino acid residues and contains 50% or more of a hydrophobic amino acid residue.

TABLE 1

| Sequence | SEQ ID: |
|---|---|
| AAAAAAAA | 1 |
| AAAAAAAAA | 2 |
| GIAAIAAAI | 3 |
| AIAAIAAAI | 4 |

The polypeptide chain of the intermediate agent preferably has the first element in the N-terminal region or the C-terminal region. In addition, preferably, the first element is present in the N-terminal region of the polypeptide chain and includes at least a non-acidic amino acid residue. Further, the first element preferably may include serine or threonine at the second or third position from the N-terminus in the sequence of the polypeptide chain. Further, in the first element, the sequence of three or two residues from the N-terminus in the sequence of the polypeptide chain is preferably selected from the residues in the following table.

TABLE 2

| Sequence of N-terminal region | IAA, VAA, FAA, PAA, AAA, LAA, QAA, IAT, ATA, FAT, WAT, VAT, LAT, AAT, PAT, IHT, IPT, IIT, IMT, IST, ITT, IQT, IAS, IGS, IVS, ISS, ITS, IQS, INS, IAY, IAE, IAI, AT |
|---|---|

According to the present invention, an intermediate agent for immobilization of a microobject which comprise at least a first element that is capable of interacting with a microobject to be immobilized on a solid-phase material may be provided. The intermediate agent is immobilized on the surface of the solid-phase material in order to immobilize the microobject on the solid-phase material. In the intermediate agent of the present invention, the microobject preferably include a polypeptide chain, and more preferably, is an antibody.

In the intermediate agent of the present invention, its molecular weight is preferably 5000 or less. In addition, the intermediate agent is preferably an organic molecule having a chain structure; more preferably includes a polypeptide chain. Additionally, the polypeptide chain preferably may comprise a first element in the N-terminal region or the C-terminal region. Moreover, the first element preferably contains at least a non-acidic amino acid residue in an N-terminal region of the polypeptide chain. Furthermore, the first element preferably has serine or threonine at the second or third position from the N-terminus of the polypeptide chain. In addition, the first element may have a sequence of two or three residue from the N-terminus of the polypeptide chain selected from the sequence in Table 2. Additionally, the polypeptide chain preferably has an α-helix structure.

The intermediate agent of the present invention can comprise a second element that can be interactive with the solid-phase material. In addition, the intermediate agent of the present invention can have an α-helix structure that contains a polypeptide chain and contains 50% or more of a hydrophobic amino acid residue. The hydrophobic amino acid residue may be selected from alanine and isoleucine. Additionally, the α-helix structure may have a hydrophobic helix structure including an amino acid sequence in which 8 or more hydrophobic amino acid residues are consecutively arranged. The hydrophobic helix structure may have amino acid sequence selected from the amino acid sequences shown in Table 1. Moreover, the polypeptide chain preferably has an amino acid residue having 12 to 20 residues.

According to the present teachings, a solid-phase body having a microobject immobilized thereon may be provided. The solid-phase body comprises a solid-phase material, any of the aforementioned intermediate agent and a microobject that is immobilized to the solid-phase material via the intermediate agent. The solid-phase material may be a photoresponsive material that contains a photoresponsive component that is capable of being deformed by light irradiation. The microobject is preferably immobilized to the solid-phase material by light irradiation in a state in which the microobjects are distributed on the surface of the solid-phase material or in its vicinity. In addition, the microobject may contain a polypeptide chain, and may also be an antibody.

BRIEF DESCRIPTION OF THE DRAWINGS

FIG. 2 shows an example of the solid phase support of the present invention.

FIG. 3 shows an example of the solid-phase body of the present invention.

FIG. 4 shows amino acid sequences of the synthetic peptides in Example 1.

FIG. 5(A) shows an α-helix structure of a synthetic peptide in Example 1, and FIG. 5(B) shows the amino acid coordination positions of a synthetic peptide in Example 1.

FIG. 10 shows evaluation results of the antibody fixability, the immobilization antibody capability and the orientation when a nonpeptidic organic polymer is used as an intermediate agent, in Example 6.

FIG. 11 shows the amino acid sequences of the synthetic peptides used in Example 7.

FIG. 13 shows the amino acid sequences of the synthetic peptides used in Example 8 as well as evaluation results of the fixability, the immobilization antibody activity and the orientation of each of these synthetic peptides.

DETAILED DESCRIPTION OF THE INVENTION

According to the method of manufacturing the solid-phase body of the present teachings, the presence of an intermediate agent having a first element that causes an interaction with a microobject on the surface of a solid-phase material enables the immobilization of the microobject to the solid-phase material in a state in which the interaction is exhibited. In other words, since the intermediate agent has the first element that can interact with the microobject, the amount of immobilization of the microobject can be increased without introduction of a special element into the microobject as well as into the solid-phase material for achieving the orientation of the microobject or for increasing the immobilization amount. According to the present teachings, at the same time as being immobilized, the microobject can be promoted in its orientation without such additional introduction of special elements.

In addition, according to the manufacturing method of the present teachings, the microobject interacts with the intermediate agent and, at the same time, is immobilized to the solid-phase material. Thus, the microobject, which avoids direct contact and interaction with the solid-phase material for orientation control, can be immobilized to the solid-phase material. This configuration is useful in reducing the effect of an element for immobilization that is contained in the solid-phase material to be imposed on the microobject and the effect of immobilization itself on the solid-phase material.

Figure 1:
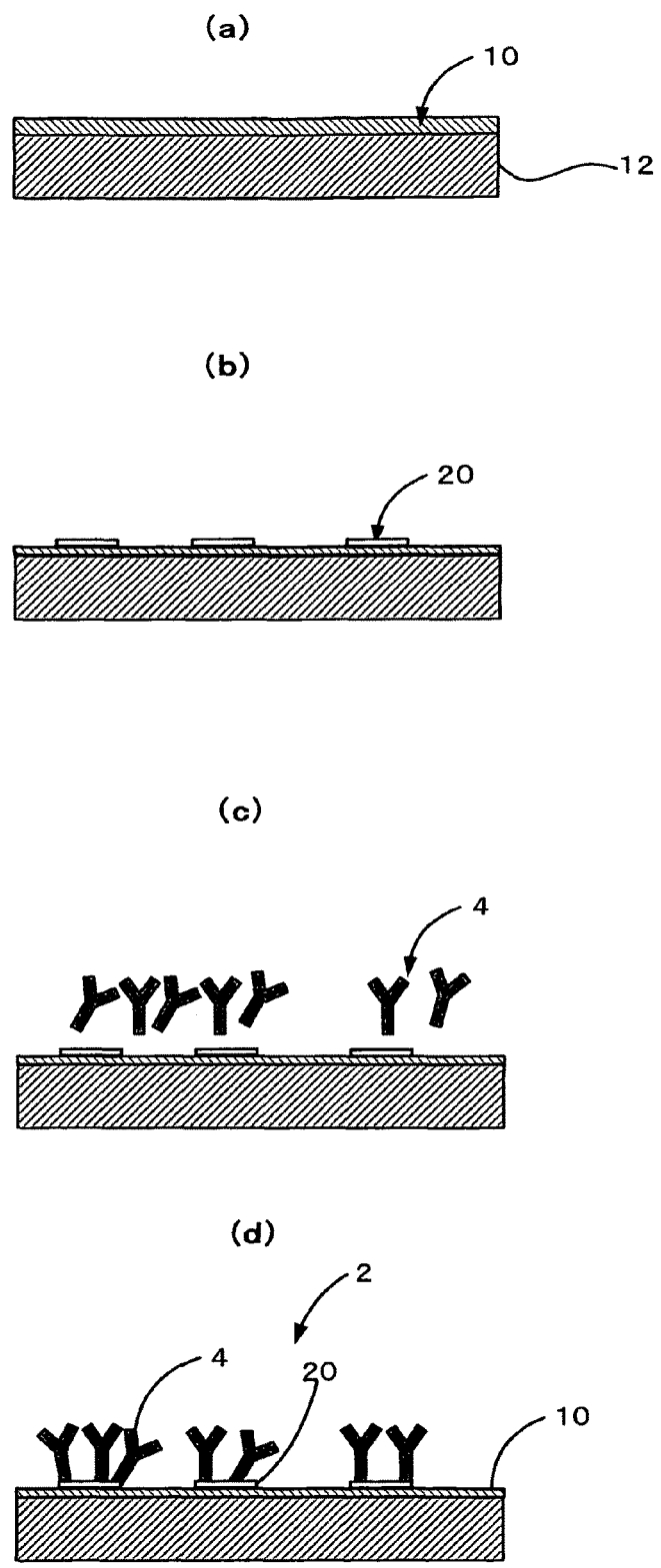
FIG. 1 shows one example of the immobilization method of the present invention.

The present teachings may also relate to a method of manufacturing a solid-phase body having a microobject immobilized thereon, a solid phase support having a microobject immobilized thereon, a solid phase support for immobilizing a microobject, a method of manufacturing a solid phase support, a variety of solid phase supports and use of a solid phase support and an intermediate agent used for immobilizing a microobject. Hereafter, embodiments of the present teachings will be described in detail with reference to drawings. FIG. 1 indicates one example of the method of immobilizing a microobject of the present teachings, FIG. 2 illustrates a solid phase support for light fixation, and FIG. 3 illustrates a solid-phase body of the present teachings.

(Method of Producing a Solid-Phase Body in which a Microobject is Immobilized to a Solid-Phase Material)

The method of producing a solid-phase body of the present teachings is, namely, a method of immobilizing a microobject to a solid-phase material. In the descriptions below, the method of producing a solid-phase body of the present teachings will be set forth in connection with a method of immobilizing a microorganism.

As shown in FIG. 1, the method of immobilizing a microobject of the present teachings comprises a solid-phase material preparatory step of a solid-phase material 10 and a microobject immobilization step of immobilizing one or a plurality of microobject 4 to the solid-phase material 10. Hereinafter, the microobject 4, the solid-phase material 10 and an intermediate agent 20 will orderly be described and then the process for immobilizing the microobject 4 will be described. Note that in the description below, immobilization of one microobject via one intermediate agent will be explained; however, according to the present teachings, a plurality of intermediate agents may be provided in the solid-phase material, and a plurality of microobjects may be immobilized onto each of the intermediate agent on the solid-phase material by the processing as described below.

(Microobject)

The kind of a microobject is not particularly limited so long as it is tangible. For example, one kind, or two or more kinds of materials that may be selected from (1) inorganic materials such as metals, metal oxides, semiconductors, ceramics, and glass, (2) organic materials such as so-called plastics, (3) biomolecular materials such as proteins, nucleic acids, saccharides and lipids, (4) composite materials made by conjugating two or more kinds of materials selected from a variety of materials of (1) to (3) listed above and the like. Among them, biomolecular materials are preferable.

(Biomolecular Materials)

Biomolecular materials that are targets of the present teachings do not mean one molecule alone; it may be a set of like molecules made of two or more molecules, or may be composites of different molecules. In addition, the biomolecular materials may also be assemblies, such as self assemblies, that are made of many like or different molecules.

The biomolecular materials are not particularly limited to, but may include molecules present in organisms such as animals, plants, microorganisms and viruses, produced by organisms or metabolized by organisms, or molecules made by artificially modifying these organisms, or artificially designed molecules not present in nature. In addition, the biomolecular materials not only include molecules collected from living things, but also may include molecules produced in living things other than organisms in which the molecules are artificially and originally present, or molecules artificially chemically synthesized outside organisms or synthesized by enzymes or the like.

The kinds of biomolecular materials include, typically, biomaterials such as polypeptides, nucleic acids, saccharides, lipids and osteogenic materials, various biological cells and their parts, and biological materials such as tissues and organisms themselves. Additionally, the biomolecular materials may be conjugated with other organic materials and/or inorganic material or the like upon being immobilized to solid phases. Of these, the biomolecular materials that are immobilized to the present solid-phase materials preferably contain a polypeptide chain respectively.

Herein, the polypeptide means a polypeptide of arbitrary size, structure or function. Hence, the polypeptides may include oligopeptides having 30 or less amino acid residues. The polypeptides include, for example, various proteins, enzymes, antigens, antibodies, lectin or cell membrane receptors. Antibodies can be preferably used as the microobject 4 containing a polypeptide chain. In addition, the antibody means a natural immunoglobulin, or a wholly or partially synthetically (artificially) produced immunoglobulin. The antibodies include all the derivatives that maintain specific binding capability. The nucleic acid may have a single strand or a double strand. The nucleic acid may contain DNA, RNA, DNA/RNA hybrids, DNA-RNA chimera, bases, and other modifiers regardless of artificial and natural ones. In addition, the chain length of the nucleic acid is not especially limited.

Additionally, the photoresponsive component and the microobject that are usable in the present teachings can utilize carriers or light fixation materials described in Japanese Patent Application Publication Nos. 2003-329682, 2004-93996, 2004-251801 and 2007-51998, the descriptions of which are herein incorporated by reference. Moreover, herein, the disclosures of Japanese Patent Application Publication Nos. 2003-329682, 2004-93996, 2004-251801, 2006-233004, 2006-321719 and 2007-51998, the descriptions of which are also incorporated herein by reference.

(Solid-Phase Material)

The solid-phase material 10 used in the immobilization method of the present teachings, the solid phase support described below and the microobject immobilization solid-phase body and the like is allowable so long as it can immobilize the target microobject 4 to the solid-phase material 10. The immobilization principle for immobilizing the microobject 4 to the solid-phase material 10 includes noncovalent interaction such as hydrogen bonding, hydrophobic interaction, hydrophilic interaction and electrostatic interaction, covalent bonding and light fixation based on optical deformation by light irradiation.

The solid-phase material 10 preferably comprises one or more element to be used for the immobilization principle for immobilizing the microobject 4 to the solid-phase material 10. In a case where electrostatic interaction is used as the immobilization principle, for example, a positive electric charge originated from amino acids such as polylysine and lysine can be possessed by the surface of the solid-phase material 10.

In a case where covalent bonding is used as the immobilization principle, a functional group that can covalently be linked to a functional group owned by the microobject 4 can be possessed by the solid-phase material 10 on its surface. For instance, the solid-phase material 10 may comprise a crosslinkable functional group that can have crosslinking reaction with a functional group possessed by the microobject 4. The kind of crosslinking functional group can be selected, depending on a functional group owned by the microobject 4 to be immobilized and an approach to be used. For instance, in cases which the microobject 4 comprises an amino group, the crosslinking functional group of the solid-phase material include a variety of crosslinking functional groups such as NHS groups, aldehyde groups and epoxy groups. In addition, in cases which the microobject 4 has a thiol radical, the crosslinking functional groups include crosslinking functional groups such as a maleimide group. Still further, in cases which the microobject 4 comprises an aromatic group, the crosslinking functional groups include a diazonium group and the like.

Moreover, even when the immobilization principle of immobilizing the microobject 4 to the solid-phase material 10 uses covalent bonding, the solid-phase material 10 itself need not necessarily comprise a functional group that can be covalently linked to the microobject 4 directly, as described above. If the solid-phase material comprises a multivalent crosslinkable compound such as a multivalent crosslinkable polymer that crosslinks the microobject 4 with the solid-phase material 10 and a functional group that can be linked to the multivalent crosslinkable compound, it can covalently bond to a functional group owned by the microobject 4 via the multivalent crosslinkable compound. The crosslinkable functional groups owned by such a multivalent crosslinkable compound include, for example, amino groups, carboxyl groups, aldehyde groups and epoxy groups. The multivalent crosslinkable compounds corresponding to these crosslinking sites include Multi-Arm PEG (available from NOF CORPORATION), EMCS and SPDP (available from DOJINDO LABORATORIES), and $BS^3$, DMS and SMCC (available from Pierce Biotechnology, Inc.).

In addition, an element such as one of the functional groups as described above for immobilization by covalent bonding of the microobject 4 and the solid-phase material 10 may be imparted to the microobject 4 that does not originally have such a functional group, so long as the imparted amount is within the range in which the activity and the like of the microobject 4 are not inhibited.

Light fixation is preferably used as an immobilization principle for the microobject 4 from the viewpoint with consideration of an effect on the microobject 4; in particular in view of activity securing when the microobject 4 is a biomolecular material. Selection of light fixation as an immobilization principle is preferred also in that a special element for orientation or the like need not be imparted to the microobject 4.

Here, light fixation means that a photoresponsive material containing a photoresponsive component that comprise the characteristic of being deformed by light irradiation is used as the solid-phase material 10, and that the microobjects 4 are distributed on or in the vicinity of the surface of the solid-phase material 10, and subjected to light irradiation to thereby immobilize the microobject to the solid-phase material 10. Although the relationship between light irradiation in light fixation and the fixation of a photoresponsive component and the microobject 4 is not necessarily clarified, the light fixation can be defined at least as a fixing approach that increases the amount of adsorption of the microobject 4 to the solid-phase material 10.

The solid-phase material 10 that makes use of light fixation has a photoresponsive component in its matrix constructing the solid-phase material 10. In the matrix of the solid-phase material 10 (parent phase), its material is not particularly limited so long as it can maintain a photoresponsive component to be capable of light fixation. For example, the matrix material can utilize various organic materials including a low molecular weight material or a polymeric material, inorganic materials such as glass and organic-inorganic composite materials, and the like. The matrix material is preferably a polymeric material or a composite material including a polymeric material, considering the dispersal and the retention capability, and the like in the matrix of a photoresponsive component.

The polymeric material constructing the matrix is not particularly limited to, but can use a variety of thermoplastics or thermoset polymers. Such polymeric materials include, for example, (1) polymers of carbon multiple bond-based monomers such as olefinic polymers, vinyl polymers, acrylic polymers, methacrylic polymers, styrenic polymers and diene polymers, (2) polymers of cyclic monomers such as cyclic ether polymers, (3) polymers of difunctional monomers such as ester polymers, urethane polymers and urea-based polymers, and the like. Of these, in consideration of the convenience of copolymerization, polymers of monomers that have a double bond (hereafter, also called double-bond monomers) such as olefinic polymers, acrylic polymers, and methacrylic polymers and urethane polymers are preferred. Double-bond monomers are more preferable. In particular, acrylic polymers, methacrylic polymers and acryl-methacryl copolymers, which have little nonspecific adsorption when a protein such as an antibody is immobilized, can effectively restrain a background signal in an antibody chip, a microreactor, or the like. In addition, urethane polymers and urethane (meth) acrylic polymers can be preferably used in the present teachings in that they can increase the amount of light deformation and also can be preferably used also when surfaces that are larger in polarity than those of acrylic polymers.

The matrix is preferably configured to generate shape deformation (hereafter, referred to as light deformation) as a result of structural molecular change of a photoresponsive component or the like caused by light irradiation. Herein, light deformation includes, in addition to shape-transform in macroscopic usual meaning, deformation due to entanglement of a microobject and the surface of a solid-phase material or the like in molecular level movement. Among such deformations, some of them cannot be observed by usual observation means due to the amount of deformation or the deformation form being subtle. Light deformation is considered to be generated by induction caused by changes in the volume, density, free volume or the like of, for example, a composite material or a photoresponsive component during light irradiation, due to the presence of the photoresponsive component in a matrix material.

(Photoresponsive Component)

The photoresponsive component is a component in which a change in molecular structure or a change in molecular disposition takes place by light. In general, a phenomenon in which a molecular structure is changed by light is called photochromism. As photoresponsive components to be used by the present teachings, compounds called photochromic compounds can be generally used. Of these, compounds that cause photoisomerization can be preferably used. In addition, compounds in which changes in molecular dispositions such as photoinduced orientations and photoassociations with or without accompaniment of molecular structural changes such as photoisomerization (in particular, anisotropic changes) can also be used as photoresponsive components of the present teachings so long as light fixation on the surface of a solid-phase material is possible.

Various components that have been used so far can be used for such light fixation as a photoresponsive component. The photoresponsive components include, for example, photoisomerization compounds including components that cause trans-cis photoisomerization such as organic compounds including azo compounds, spiropyran compounds, spirooxazine compounds and diarylethene compounds, and inorganic compounds generally called chalcogenite glass.

The photoresponsive components preferably include compounds (i.e. azo compounds) having a dye structure that has an azo group (—N=N—). The azo compound causes trans-cis isomerization by light irradiation or the like. Molecular level movement by this isomerization makes a matrix material plastisized, thus making deformation easy. In particular, amino-type azobenzene compounds having a structure of aminoazobenzene or its derivative are preferred. Amino-type azobenzene compounds can be typically expressed by Formula 1 as below.

[Formula 1]

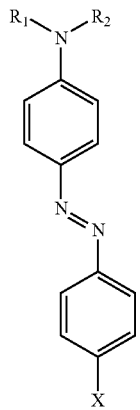

formula 1

In the above formula, $R_1$ and $R_2$ each independently represent a hydrogen atom and a substituent, and X represents a hydrogen atom, an electron withdrawing substituent or an electron-releasing substituent.

Here, the substituent of $R_1$ and $R_2$ can indicate alkyl groups, hydroxyalkyl groups, halogen atoms, nitro groups, amino groups, carboxyl groups, aryl groups, allyl groups, alkyl ester groups, alkyl ether groups, alkylamino groups, alkylamide groups, isocyanate groups and epoxy groups, etc. In particular, when one of the substituent in $R_1$ and $R_2$ is an acrylic compound such as acrylic acid or (meth)acrylic acid that has a polymerizable double bond or the like in its terminal or another double-bond component, Formula 1 can represent a double-bond monomer or a photoresponsive polymer comprising a polymerizable group derived from the double-bond component. In addition, when one of the substituents in $R_1$ and $R_2$ is a polymerizable component of condensation polymerization or addition polymerization such as an isocyanate group, an amino group, a carboxyl group, or a hydroxyl group, Formula 1 represents, in addition to the addition polymerizable polymer, a photoresponsive polymer comprising a polymerizable group derived from the polymerizable component (polymer having an azo dye-containing unit). In consideration of the deformability of a photoresponsive material, the polymer skeleton of a photoresponsive material is preferably a (meth)acrylic polymer, an urethane polymer or an urethane-acrylic polymer, and therefore the photoresponsive component of the present teachings is preferably a (meth)acrylic monomer, an urethane monomer or a polymer containing them ((meth)acrylic polymer, urethane polymer or urethane-acrylic polymer).

Furthermore, the electron withdrawing substituents in X include, for example, a cyano group, a nitro group, a sulfonic group, and the like. Moreover, the electron-releasing substituents include, for example, an amino group, a dimethylamino group, an alkyl group, and the like. Substances made by binding such substituents are preferred since the matrix material is considered to have a large plasticizing action by repetition of cis-trans isomerization during light irradiation. The photoresponsive components that are azo compounds can be used in combination of one kind or two kinds or more.

Although such a photoresponsive component may be introduced into a matrix as a component other than a matrix material, it is preferably present in a part of the matrix material (main chain or side chain) via a chemical bond. In addition, the photoresponsive component is preferably uniformly present in the matrix. A microobject can be immobilized at a desired part on the surface of a solid-phase material by such a uniform distribution of the photoresponsive component.

Moreover, in a case where, hydrogen bonding, hydrophobic interaction, hydrophilic interaction, or the like is used as an immobilization principle for the microobject 4, a suitable functional group or treatment can be each applied to the solid-phase material 10. An approach for this is well-known to those skilled in the art. Moreover, a part in which an inherent immobilization principle in the solid-phase material 10 is exhibited may only be at least on the surface layer of the solid-phase material 10. A layer for such immobilization may also be carried on a suitable support.

The three-dimensional morphology of the solid-phase material 10 is not especially limited. A various shapes such as a spherical shape, an infinite form, a needle shape, a rod shape and a flake shape can alternately be taken in addition to a film form, a sheet form and a plate form. The impartment of an immobilized layer to the surface layer of a support can be carried out by a known method such as spin coating, dip coating or inkjetting.

The solid-phase material 10 may comprise an element for immobilizing the intermediate agent 20 to be described below to the solid-phase material 10 besides an element for the immobilization principle for immobilizing the microobject 4. Such an element can be adopted by being selected from elements which the solid-phase material 10 can comprise for immobilizing the microobject 4 described above. The element for fixing the intermediate agent 20 varies depending on the kind of intermediate agent 20. However, the element may be identical to or different from the inherent immobilization principle for immobilizing the microobject 4.

Therefore, the solid-phase material 10 can also comprise elements for two or more kinds of immobilization principles of an element for immobilizing the microobject 4 and an element for immobilizing the intermediate agent 20. For instance, the solid-phase material 10 can comprise a certain kind of crosslinkable functional group for immobilizing the microobject 4 and another kind of crosslinkable functional group for immobilizing the intermediate agent 20. Where the microobject 4 can be immobilized to the intermediate agent 20 by different immobilization principles, when the microobject 4 is immobilized to the solid-phase material 10 after the microobject 4 is oriented by the intermediate agent 20, the immobilization operation of the microobject 4 does not affect the immobilization state of the intermediate agent 20, whereby an intended orientation state for the microobject can be obtained easily and surely.

Moreover, the solid-phase material 10 can also comprise the same element of the immobilization principle for immobilizing the microobject 4 and the intermediate agent 20. For example, in a case where both the microobject 4 and the intermediate agent 20 are immobilized to the solid-phase material 10 by light fixation, the solid-phase material 10 may only comprise a single kind of a photoresponsive component for these immobilization elements. In addition, the inclusion of two or more kinds of photoresponsive components in the solid-phase material 10 also makes it possible to immobilize the microobject 4 and the intermediate agent 20 even by light irradiation in different wavelength regions.

Additionally, the solid-phase material 10 may not necessarily comprise an element for immobilizing the intermediate agent 20. For instance, the intermediate agent 20 can be immobilized to the solid-phase material 10 by mere coating or the like, and also use of heat or pressure or the like enables the intermediate agent 20 to be immobilized to the solid-phase material 10.

(Intermediate Agent)

The intermediate agent 20 at least has a first element that can interact with the microobject 4. The intermediate agent 20, if comprising the first element, can bind the microobject 4 by interaction, thereby being capable of the oriented immobilization and an increase in the amount of immobilization, of the microobject 4.

(First Element)

The interactions that are caused between the first element and the microobject 4 are not especially limited and may simply include noncovalent interactions such as an electrostatic interaction, an ionic bond, a hydrogen bond, a dipole interaction, a hydrophobic interaction and a hydrophilic interaction. In addition, the interaction may include interaction in vivo such as interactions of various intermaterials of antigen-antibody, substrate-enzyme, ligand-receptor, nucleic acid hybridization and nucleic acid-protein. The interactions in the first element may also be a single interaction of such various interactions and may also be interactions in combination of two kinds or more. Additionally, the first element may also include one element or two or more elements in the intermediate agent 20. The interaction that is caused by the first element can preferably use an electrostatic interaction or a hydrophilic interaction. These interactions are advantageous for being caused between biomolecular materials that especially have a polypeptide chain or the like as the microobject 4.

The first element is preferably an element that exhibits an electrostatic interaction. An element that causes an electrostatic interaction may have, for example, a negative charge and may also have a positive electric charge. Such first elements include an acidic functional group that generates a negative electric charge and a basic functional group that generates a positive electric charge. The acidic functional groups are not particularly limited to, but include a carboxyl group, a sulfone group and a phosphate group, preferably a carboxyl group. The basic functional groups include amino groups such as a primary amino group, a secondary amino group and a quaternary ammonium group, preferably amino groups such as a primary amino group.

(Second Element)

The intermediate agent 20 may comprise a second element that is able to interact with the solid-phase material 10. The inclusion of the second element enables the intermediate agent to interact with the solid-phase material 10, and enables the intermediate agent 20 itself to be orientation-immobilized to the solid-phase material 10, thus being capable of certainly orientation-immobilizing the microobject 4 to the solid-phase material 10. In addition, the first element can be easily oriented and exposed to the microobject 4 by being able to orient the intermediate agent 20 to the solid-phase material 10, so that the amount of immobilization of the microobject 4 can also be increased. In particular, in a case where the principle for immobilizing the intermediate agent 20 to the solid-phase material 10 is light fixation, coating or the like, and is not one of those principals that immobilize the intermediate agent to the solid-phase material 10 in a specific site, the inclusion of such a second element in the intermediate agent makes the intermediate agent 20 to easily orient and immobilize on the surface of the solid-phase material 10.

The interaction caused between a second element and the solid-phase material 10 is not specifically limited and can be properly selected from interactions similar to those of the first element. The interaction exhibited by the second element may be the same as or different from the interaction exhibited by the first element; it is preferably different from the viewpoint of the orientation control of the intermediate agent 20 itself and the microobject 4. In addition, the interactions in the second element may also be a single interaction of such various interactions and may also be interactions in combination of two kinds or more. Additionally, the second element may also include one element or two or more elements in the intermediate agent 20.

The second element is an element that causes a hydrophobic interaction, considering the property and the like of the general solid-phase material 10. Such second elements can be made of, for example, hydrocarbon groups including alkyl groups such as methyl groups and ethyl groups or aromatic functional groups such as phenyl groups and naphthyl groups.

In a case where the intermediate agent 20 comprises such second element, the combination of the first and second elements in the intermediate agent 20 may adopt any combination among the selection of respective elements. The combination may be e.g. a combination of a hydrophilic interaction and a hydrophobic interaction, or a combination of an electrostatic interaction and a hydrophobic interaction. These combinations may also be properly determined depending on the relationship between the microobject 4 and the solid-phase material 10.

(Hydrophilic Region and Hydrophobic Region)

The intermediate agent 20 preferably comprises a hydrophilic region and/or a hydrophobic region. These regions may be included as one or both of the first and second elements, or may also be included as a region different from these elements. For example, the hydrophilic region may also be the first element or the second element or both in the intermediate agent 20. In addition, the hydrophobic region may also be the first element or the second element or both. The hydrophilic and hydrophobic regions each exhibit hydrophilic and hydrophobic interactions between the microobject 4 and the solid-phase material 10 and also can contribute to the stability of the intermediate agent 20, the orientation of the intermediate agent 20 itself to the solid-phase material 10 and the microobject 4 and the like in an immobilization environment in which the microobject is immobilized to the solid-phase material or in an environment of use of a solid-phase body having immobilized thereon the microobject 4. Moreover, the regions stabilize the respective dispositions and mutual position relation of the first and second elements in the intermediate agent 20, thereby being expected to easily control the orientation of the microobject 4.

As described above, although the solid-phase material 10 can comprise an element for immobilizing the intermediate agent 20, the intermediate agent 20 can also comprise an element for immobilizing itself to the solid-phase material 10. Such an element can adopt an element capable of comprising the solid-phase material 10 or the microobject 4 for the immobilization principle between the microobject 4 and the solid-phase material 10, described above. Such an element that the intermediate agent 20 comprises may also be identical to or different from the same element as an element capable of being included by the solid-phase material 10 or the microobject 4 for the immobilization principle of the microobject 4. For example, when covalent bonding is adopted as the immobilization principle for fixing the intermediate agent 20, covalent bonding due to another kind of a crosslinkable compound as an element for immobilizing the intermediate agent 20 is preferably adopted, and the intermediate agent 20 can comprise an element for such reaction.

In addition, even though no special element is imparted to both the solid-phase material 10 and the intermediate agent 20, both the materials can be linked to each other by supplying a compound that introduces a covalent bond into therebetween, depending on the kind of functional groups or the like included by each of the intermediate agent 20 and the solid-phase material 10.

The intermediate agent 20 comprises a first element and its constituent material is not limited, so long as the intermediate agent can be immobilized to the solid-phase material 10 by an inherent immobilization principle between the intermediate agent and the solid-phase material 10 even if the intermediate agent interacts with the microobject 4. The intermediate agent 20 can properly select and use an organic compound having a covalent bond between carbon atoms and/or a covalent bond between a carbon atom and a nitrogen atom, inorganic molecules complex molecules (organic-inorganic composite materials).

The organic molecules as the intermediated agent 20 include, for example, various organic compounds in addition to a variety of derivatives of polypeptide chains including natural polypeptide chains or modified amino acids, various derivatives including nucleic acids such as DNA and RNA and modified bases, lipids, polysaccharides, surfactants, and organic polymers. Additionally, the inorganic molecules include metal simple substances, metal clusters, metal compounds, and the like. The intermediate agent 20 is properly selected according to an interaction to be exhibited between the microobject 4 and the first element and further an interaction to be exhibited between the microobject 4 and the second element, as necessary. Preferably, the organic molecule is used as the intermediate agent 20. The intermediate agent 20 being consisted of organic molecule easily exhibits the intended interaction.

The structure of the intermediate agent 20 can preferably have a linear or branched chain structure. Such the intermediate agent 20 readily imparts anisotropy to a molecule, thus being capable of easily imparting the first and second elements. For example, if the intermediate agent 20 comprises a linear chain structure, the first element is imparted to one end or its end part, and the second element can be imparted to the other end or its end part. In addition, a plurality of the first and second elements can be imparted by branching from a different part of the linear chain structure. Additionally, the first and second elements can also be imparted to a plurality of ends of the branched chain structure. Preferably, the intermediate agent 20 has a linear chain structure.

Preferably, the intermediate agent 20 is an organic molecule that has a chain structure. In other words, the organic molecules include a variety of derivatives of polypeptides including polypeptide chains and modified amino acids, various derivatives including nucleic acids such as DNA and RNA and modified bases, lipids, polysaccharides, surfactants, and organic polymers, and the like. The chain structure may be linear or branched, preferably have a linear structure, more preferably a single-stranded structure. When the intermediate agent 20 is an organic molecule and has a linear structure, the intermediate agent 20 has a high degree of freedom for the position, the range and the kind of interaction of the first element and the position, the range and the kind of interaction of the second element. For example, the first element based on electrostatic interaction can be imparted to one end or its end part, and the second element based on a different interaction, for instance, a hydrophobic interaction can be readily imparted to the other one end or the other end part.

The intermediate agent 20 preferably has at least a polypeptide chain as an organic molecule. That is, the intermediate agent 20 is preferably a polypeptide chain as individual material or a composite of a polypeptide chain and another molecule. The polypeptide chain has a chain structure and, specifically, a typical organic molecule that has a linear structure. The polypeptide chain can easily impart the first and second elements that exert electrostatic interaction, hydrogen bonding, hydrophobic interaction, hydrophilic interaction and the like to the intermediate agent 20, on the basis of the characteristics possessed by various amino acid residues. Moreover, the hydrophilic and hydrophobic regions can be easily constructed with amino acid residue compositions of polypeptide chains. In addition, polypeptide chains can construct rigid second structures including a helix structure such as an α-helix and a sheet structure such as a β-sheet and exhibit dipole interaction and the like on the basis of the second structure to be capable of exerting further selective interaction to the microobject 4 and the solid-phase material 10, thereby being able to improve the amount of immobilization and orientation of the microobject 4.

Additionally, the intermediate agent 20 may have a material similar to or different from the microobject 4. For instance, when the microobject 4 contains a polypeptide chain, the polypeptide chain can be included in the intermediate agent 20, or the intermediate agent 20 may be a surfactant that does not contain a polypeptide chain.

(Molecular Weight)

The molecular weight of the intermediate agent 20 is within the range in which the effect by the intermediate agent 20 and the fixability of the microobject 4 by the solid-phase material 10 are maintained. The molecular weight of the intermediate agent 20 is preferably 5000 or less. The molecular weight of the intermediate agent 20 is more preferably 3000 or less. In addition, the molecular weight of the intermediate agent is preferably 1/10 or less of the molecular weight of the microobject 4 in the relation to the molecular weight of the microobject 4. This is because, when the molecular weight of the intermediate agent 20 greatly exceeds 1/10 of the molecular weight of the microobject 4, the immobilization is likely to be prevented. The molecular weight of the intermediate agent 20 is, although depending on the molecular weight of the microobject 4, more preferably 1/20 or less of the molecular weight of the microobject 4. Note that the expression 'intermediate agent has a sufficiently small molecular weight as compared with the molecular weight of the microobject' may include all or one of the criteria as hereinstated but not limited thereto. Moreover, the term may also include the approximate range thereof.

The intermediate agent 20 may have a material similar to or different from the microobject 4. For instance, when the microobject 4 contains a polypeptide chain, the intermediate agent 20 can be made to be a polypeptide, or also made to be a surfactant.

A preferred embodiment as the intermediate agent 20 is described more specifically on the basis of the various aspects of the intermediate agent 20 as described above. The intermediate agent 20 to be described below can be preferably used to immobilize the microobject 4 made up of a polypeptide chain or has a polypeptide chain, but the immobilization target is not especially limited. Additionally, the solid-phase material 10 is preferably a hydrophobic material, in consideration of the characteristics and the like of a polypeptide; however, it is not limited thereto. The solid-phase material 10 and the immobilization principle are preferably a photoresponsive material and light fixation, from the viewpoint of being capable of stably immobilizing the microobject 4.

When the intermediate agent 20 has a polypeptide chain, the first element may be present in the N-terminal region, or be present in the C-terminal region, of the polypeptide chain, or both. Moreover, the intermediate agent 20 preferably comprises an element, such as the first element that can exhibit an electrostatic interaction or an element that can exhibit an hydrophilic interaction between the intermediate agent 20 and the microobject 4. In a case where the first element can exhibit an electrostatic interaction, the microobject 4 comprising an electric charge, particularly a polypeptide chain, can be effectively oriented and also its amount of immobilization can be increased. In addition, in a case where the first element can exhibit a hydrophilic interaction, the element can effectively orient the microobjects 4 such as an enzyme or an antibody that exposes a hydrophilic chain on their surfaces. The first element is more preferably an element that can exhibit an electrostatic interaction.

The first element that can exhibit an electrostatic interaction preferably comprises a positive electric charge. A positive electric charge is preferably imparted by amino group ($NH_3^+$). A positive electric charge is preferably included in the end of the intermediate agent 20. When the intermediate agent 20 comprises a second element, the second element is preferably included in the other end.

When the intermediate agent 20 that has a polypeptide chain has an amino group as a first element that exhibits an electrostatic interaction, the amino group is included as an organic group that configures a part of intermediate agent 20. Preferably, the amino group is included as an amino acid residue in the polypeptide chain, more preferably in the N-terminus. An amino group of an amino acid residue of the N-terminus is not involved in a peptide bond, so that the amino group is dissociated into a cation according to a surrounding pH and positively charged. The amino acid is usually dissociated into a cation in a neutral neighborhood.

The amino acid residue that donates a positive electric charge is unpreferably an acidic amino acid residue having an additional carboxyl group like glutamic acid and aspartic acid from the viewpoint of not offsetting the positive electric charge. In other words, the amino acid residue is preferably a non-acidic amino acid residue other than the acidic amino acid residues.

Moreover, the amino acid residue that donates a positive electric charge can be any of hydrophobic amino acid residue selected from isoleucine, valine, phenylalanine, proline, alanine, leucine and phenylalanine. The amino acid residue is more preferably any residue selected from isoleucine, valine, alanine, phenylalanine and tryptophan, from the viewpoint of the orientation control of the microobject 4. Isoleucine is preferable from the viewpoint of the orientation control and fixability of the microobject 4.

In addition, when a positive electric charge is included in an N-terminus, preferably, any of serine, threonine, isoleucine, alanine, tyrosine and tryptophan is present within 3 residues (second residue or the third residue, preferably the third residue) from the N-terminus, more preferably any of serine, alanine and threonine, still more preferably any of serine and threonine comprising a hydroxyl group, most preferably threonines. Additionally, in the N-terminus comprising a positive electric charge and its vicinity (preferably, the second position from the N-terminus), no presence of acidic amino acid residues comprising additional carboxyl groups such as glutamic acid and aspartic acid is preferred. That is, a non-acidic amino acid residue is preferably disposed in the position.

Such an N-terminal structure is effective particularly when the microobject 4 contains a polypeptide chain and more effective when an antibody is contained therein.

When the microobject 4 contains a polypeptide chain such as an antibody, preferable N-terminal amino acid sequences are shown in the following table. In the following table, the sequences listed in the upper are sequences that promote orientation and immobilization, the sequences listed in the intermediate are sequences that exhibit high orientation in the sequences listed in the upper, and the sequences shown in the lower are sequences that exhibit high fixability in the sequences listed in the below table.

TABLE 3

| High fixabilty and high orientation | IAA, VAA, FAA, PAA, AAA, LAA, QAA, IAT, ATA, FAT, WAT, VAT, LAT, AAT, PAT, IHT, IPT, IIT, IMT, IST, ITT, IQT, IAS, IGS, IVS, ISS, ITS, IQS, INS, IAY, IAE, IAI |
|---|---|
| Higher orientation | IAT, ITT, ITS, IAS |
| Higher fixability | IPT, IMT, IST, IQT, IQS, INS |

When the intermediate agent 20 comprises hydrophobic regions described below, a first element may configure its end as a part of the hydrophobic regions or may be connected to the end of the hydrophobic region. For example, when the hydrophobic region has an α-helix structure having a hydrophobic amino acid residue, the first element may form the α-helix structure together with these polypeptide chains to configure its N-terminal region, or may be connected to the N-terminus of the α-helix structure.

The intermediate agent 20 preferably comprises a hydrophobic region. The possession of a hydrophobic region enables the hydrophobic interaction with the solid-phase material 10 that exhibits hydrophobicity on the surface of the material 10, whereby the orientation and the immobilization of the intermediate agent 20 to the solid-phase material 10 including a photoresponsive material or the like by a hydrophobic interaction are promoted. Moreover, the disposition of the first element that exerts a hydrophilic interaction and an electrostatic interaction in the intermediate agent 20 can also be stabilized. When the surface of the solid-phase material 10 exhibits hydrophobicity, the hydrophobic region of the intermediate agent 20 interacts with the solid-phase material 10 as the second element, being capable of contributing to the orientation and the immobilization of the microobject 4 via the intermediate agent 20.

When the intermediate agent 20 contains a polypeptide chain, the hydrophobic region can be an amino acid sequence in which a number of hydrophobic amino acid residues (isoleucine, valine, leucine, phenylalanine, methionine, alanine, glycine, tryptophan and proline) are dominantly present in the constituent amino acid residue composition. In other words, the hydrophobic region preferably has an amino acid sequence in which 50% or more of the total of the constituent amino acid residues are the hydrophobic amino acid residues. The proportion of the hydrophobic amino acid residues is more preferably 60% or more, still more preferably 70% or more, further more preferably 80% or more, most preferably 90% or more. In addition, as described below, in consideration of the formation of an α-helix structure, amino acid residues are preferably selected from isoleucine, valine, leucine, phenylalanine, methionine, alanine and tryptophan as a hydrophobic amino acid residue, The hydrophobic region contains more hydrophobic amino acid residues selected from, alanine and isoleucine.

Additionally, The hydrophobic region preferably contains more amino acid residues selected from neutral amino acid residues such as cysteine, threonine, serine, tyrosine, glutamine and asparagine as the amino acid residues other than the hydrophobic amino acid residues.

Such a hydrophobic region preferably contains 9 or more residues in the number of amino acid residues, considering the formation of an α-helix structure to be described below. Moreover, this hydrophobic region preferably has a total molecular weight (total molecular weight in terms of amino acid) of 700 or more in terms of amino acid in place of constituent amino acid residue.

In addition, such a hydrophobic region of the intermediate agent 20 can have, in view of its property as a polypeptide chain, the secondary structures of the α-helix or the β sheet; the hydrophobic region preferably has an α-helix structure. The intermediate agent 20 has a very stable secondary structure, thereby allowing the first element to be stably placed as well as allowing the hydrophobic interaction to be surely retained and exhibited. Additionally, the α-helix structure as the hydrophobic region is preferably rich in hydrophobic amino acid residues on one side of the α-helix structure in a spiral direction. Predominant arrangement of hydrophobic amino acid residues on one side of the α-helix structure renders it possible to cause a stable hydrophobic interaction and enhance the orientation of the intermediate agent 20 to the solid-phase material 10.

Here, in an α-helix structure of a polypeptide, when two rotations of α-helix are considered to be one wheel, a wheel model shown in FIG. 5(B) can be constructed. For example, in this model, in the amino acid residue composition coordinated in positions on one side of the α-helix, below (a, b, e, f) or above (c, d, g) in the drawing, the amount of hydrophobic amino acid residues (isoleucine, valine, leucine, phenylalanine, methionine, alanine and tryptophan) is 80% or more, and more preferably the α-helix structure as a hydrophobic region having a proportion of 90% or more of an amino acid sequence is preferred. It is more preferred that alanine, leucine and isoleucine that readily construct the α-helix structure be predominantly used for the hydrophobic amino acid residues in the amino acid sequence. Still more preferably, alanine and isoleucine are used predominantly, and most preferably, only alanine and isoleucine are used.

The α-helix structure as the hydrophobic region includes the α-helix structure having, sequence of most preferably 7 or more, or preferably 8 or more, further more preferably 9 or more of continuous hydrophobic amino acid residues. More preferably, the sequence is consisted of alanine residues and isoleucine residues.

Preferable hydrophobic regions in the cases which the intermediate agent 20 has a polypeptide chain include the following sequences comprising 8 or 9 amino acids. Most preferably, the hydrophobic region includes sequence of AIAAIAAAI.

TABLE 4

| Sequence | SEQ ID: |
|---|---|
| AAAAAAAA | 1 |
| AAAAAAAAA | 2 |
| GIAAIAAAI | 3 |
| AIAAIAAAI | 4 |

Such a hydrophobic region is preferably positioned in the end of the other side of the first element of the intermediate agent 20. When the intermediate agent 20 contains a polypeptide chain, such a hydrophobic region is preferably positioned in the C terminal region of the polypeptide chain and more preferably configures the C terminus of the polypeptide chain.

In addition, although a polypeptide chain as the intermediate agent 20 can have the α-helix structure at least in its part as the above-described hydrophobic region, it may comprise the α-helix structure by including the first element as a whole.

Although the intermediate agent 20 can comprise such a first element and a hydrophobic region, whereas the whole thereof is configured of polypeptide and comprises such a first element and a hydrophobic region therein, more preferably in cases which the intermediate agent is configured of a first element and a hydrophobic region, it is preferable that there exist 12 or more amino acid residues as a whole. Additionally, the upper limit in the aforesaid number is not especially limited, but the intermediate agent preferably has 20 or less residues, from the viewpoint that a molecular weight of 5000 or less is suitable in order to restrain steric hindrance for light fixation and from viewpoint of synthesis efficiency for chemical synthesis. The polypeptides having the following amino acid sequences can be preferably used as the intermediate agent 20.

TABLE 5

| Amino acid Sequence | SEQ ID NO |
|---|---|
| IAA AIAAIAAAI | 5 |
| VAA AIAAIAAAI | 6 |
| FAA AIAAIAAAI | 7 |
| PAA AIAAIAAAI | 8 |
| AAA AIAAIAAAI | 9 |
| LAA AIAAIAAAI | 10 |
| QAA AIAAIAAAI | 11 |
| IAT AIAAIAAAI | 12 |

TABLE 5-continued

| Amino acid Sequence | SEQ ID NO |
|---|---|
| ATA AIAAIAAAI | 13 |
| FAT AIAAIAAAI | 14 |
| WAT AIAAIAAAI | 15 |
| VAT AIAAIAAAI | 16 |
| LAT AIAAIAAAI | 17 |
| AAT AIAAIAAAI | 18 |
| PAT AIAAIAAAI | 19 |
| TAT AIAAIAAAI | 20 |
| IHT AIAAIAAAI | 21 |
| IPT AIAAIAAAI | 22 |
| IIT AIAAIAAAI | 23 |
| IMT AIAAIAAAI | 24 |
| IST AIAAIAAAI | 25 |
| ITT AIAAIAAAI | 26 |
| IQT AIAAIAAAI | 27 |
| IAS AIAAIAAAI | 28 |
| IGS AIAAIAAAI | 29 |
| IVS AIAAIAAAI | 30 |
| ISS AIAAIAAAI | 31 |
| ITS AIAAIAAAI | 32 |
| IQS AIAAIAAAI | 33 |
| INS AIAAIAAAI | 34 |
| IAY AIAAIAAAI | 35 |
| IAE AIAAIAAAI | 36 |
| IAI AIAAIAAAI | 37 |

Moreover, the intermediate agent 20 that has a polypeptide chain may comprise α-helix structure that does not have a hydrophobic region.

Next, a step of immobilizing the microobject 4 to the solid-phase material 10 will be described. Furthermore, in the following descriptions, this step will be divided into a step of preparing a solid-phase material, a step of immobilizing an intermediate agent and a step of immobilizing a microobject and will be described.

(Step of Preparing Solid-Phase Material)

When the microobject 4 is immobilized to the solid-phase material 10 with the intermediate agent 20 being interposed, first, the solid-phase material 10 is prepared as shown in FIG. 1(*a*). In an example illustrated in FIG. 1(*a*), the solid-phase material 10 is formed on the surface layer of the substrate-shaped carrier 12 as a laminar layer for immobilizing.

(Step of Immobilizing Intermediate Agent)

Next, as shown in FIG. 1(*b*), the intermediate agent 20 is supplied to the surface of the solid-phase material 10 in such a manner that the intermediate agent 20 is made present between the solid-phase material 10 and the microobject 4. Preferably, the intermediate agent 20 is immobilized to the surface of the solid-phase material 10.

The intermediate agent 20 may be dispersed on the surface of the solid-phase material 10 and immobilized, or may be immobilized to an unspecified region of the solid-phase material 10 surface, namely, to the whole surface of the solid-phase material. Alternatively, it may be immobilized according to a specific pattern. Conventionally well-known various coating processes and printing processes (including inkjetting) can be used as the approach to supply the intermediate agent 20 to the solid-phase material 10 surface. In addition, a conventionally well-known approach can be adopted also for patterning the intermediate agent 20. One example of patterning involves being able to supply a spot of a droplet of the intermediate agent 20 in an array form.

An appropriate approach can be selected according to the kind of the solid-phase material 10 and the kind of an element, which the intermediate agent 20 might comprise, for immobilization to the solid-phase material 10, to immobilize the intermediate agent 20 to the surface of the solid-phase material 10. The approach may be simply adherence along with drying or evaporation of the solvent or may apply pressure. Additionally, an element for their immobilization which the intermediate agent 20 and/or the solid-phase material 10 comprises may be used. Moreover, the approach may use a separate, suitable binder component.

When the intermediate agent 20 comprises a second element, the intermediate agent 20 is readily immobilized to the solid-phase material 10. In addition, its inclusion of the second element makes it possible for the intermediate agent itself to be oriented and immobilized.

The intermediate agent 20 may be immobilized to the solid-phase material 10 by the same immobilization principle as that by immobilizing the microobject 4 to the solid-phase material 10. This enables the step to be made simple and also can omit an element for immobilization of the intermediate agent 20 which the solid-phase material 10 should comprise. Such an immobilization principle is preferably light fixation. Use of light fixation enables immobilization merely by light irradiation even during respective immobilizations of the intermediate agent 20 and the microobject 4 and also can reduce the immobilizations of the intermediate agent 20 and the microobject 4.

(Step of Immobilizing Intermediate Agent by Light Fixation)

When a photoresponsive material is used as the solid-phase material 10, the intermediate agent 20 is preferably subjected to light fixation. In light fixation, the intermediate agent 20 is supplied to the surface of solid-phase material 10 that is a photoresponsive material or its vicinity, and the intermediate agent 20 is immobilized to the surface of the solid-phase material 10 by light irradiation.

Upon light fixation of the intermediate agent 20, the supply of the intermediate agent 20 to the solid-phase material 10 is not particularly limited to, but the intermediate agent is preferably applied to the solid-phase material in a dissolved or suspended state via a liquid medium. This is because that utilization of a liquid medium makes it possible to readily develop the intermediate agent 20 to the surface of the solid-phase material 10 and also that the intermediate agent 20 can be immobilized while maintaining its structure (e.g., when the intermediate agent 20 is a polypeptide, or the like, and its secondary structure or the like).

Moreover, the liquid medium is particularly preferably a liquid composition that is water or a medium mainly containing water. The liquid composition that is a medium mainly containing water is properly selected according to the kind of the intermediate agent 20 and examples include water, a buffer solution and a buffer solution the pH of which is adjusted. In addition, a liquid medium that improves the interaction of the intermediate agent 20 and the solid-phase material 10 can be selected as the liquid medium. For example, adjustment of the pH, electrolyte concentration, polarity or the like of the liquid medium permits the interaction to be improved. Such liquid media may include water, aqueous solvents that are organic solvents compatible with water, nonaqueous solvents alone or combinations of nonaqueous solvents, and the like. Additionally, a component necessary for imparting the liquid properties in order to improve the interaction of the solid-phase material 10 and the intermediate agent 20 may be added. Moreover, a surfactant may be added to the liquid medium for instance.

After the intermediate agent 20 is supplied to the solid-phase material 10, the irradiation of the intermediate agent 20 on the surface of the solid-phase material 10 with light renders it possible to immobilize the intermediate agent 20 to the surface of the solid-phase material. The method of light irradiation for light fixation is not especially limited. Arbitrary light such as various propagation lights, near-field lights or evanescent lights may be simply radiated so as to reach the surface of the solid-phase material 10 where the intermediate agent 20 is present, or within its vicinity. In addition, light irradiation can be selectively performed partially on the solid-phase material 10 by using a well-known approach. Moreover, a laser trapping can also be used.

The wavelength region to be used for light fixation suffices to be a wavelength region in which the molecular structure or the molecular disposition is changed in a photoresponsive component. Information on such a wavelength region can be ascertained when various available photoresponsive components can be easily obtained or are used.

Additionally, irradiation light and methods of light irradiation having already described in Japanese Patent Application Publication Nos. 2003-329682, 2004-93996 and 2004-251801 can be adopted about light irradiation for light fixation. Light fixation is disclosed in Japanese Patent Application Publication Nos. 2003-329682, 2004-93996 and 2004-251801 by these applicants and the methods can also be applied to light fixation in the present teachings.

Moreover, after the light fixation of the intermediate agent 20, preferably, the surface of the solid-phase material 10 is cleaned and the intermediate agent 20 not immobilized and the like are removed.

(Step of Immobilizing Microobject)

Next, as shown in FIG. 1(c), the microobject 4 is supplied to a region where the intermediate agent 20 on the surface of the solid-phase material 10 is disposed and the microobject 4 is immobilized to the solid-phase material 10 on the basis of the immobilization principles of the microobject 4 and the solid-phase material 10. At this time, the intermediate agent 20 comprises a first element that is capable of interacting with the microobject 4, and therefore the microobject 4 is likely to approach the region where the intermediate agent 20 is present. In addition, the microobject 4 is endowed with properties so as to be able to interact with the first element of the intermediate agent 20 and thereby achieve a constant orientation. In such a state, the microobject 4 is immobilized to the surface of the solid-phase material 10 by the immobilization principle between the two, for example, covalent bonding, electrostatic interaction, light fixation, or the like. This makes the microobject 4 be immobilized to the solid-phase material 10 with the effects of the solid-phase material 10 being avoided or restrained, as shown in FIG. 1(d). That is, the solid-phase body 2 in which the microobject 4 is immobilized to the solid-phase material 10 through the intermediate agent 20 can be obtained.

Additionally, the microobject 4 is constantly oriented on the surface of the solid-phase material 10 and immobilized as a result of an interaction cause by the first element owned by the intermediate agent 20. In particular, when the intermediate agent 20 comprises a second element, the microobject 4 can be controlled in orientation with respect to the solid-phase material 10 with great accuracy since the intermediate agent 20 is immobilized to the solid-phase material 10 in a constant orientation. Moreover, the amount of immobilization of the microobject 4 to the solid-phase material 10 is increased due to the first element. According to the method of the present teachings, addition of an element for orientation control to the microobject 4 is avoided because of the use of the intermediate agent 20 comprising the first element. Because of this, the microobject 4 can be easily oriented, and also the effects of such an additional element on the activity and the stability of the microobject 4 are decreased.

In addition, the intermediate agent 20 is present between the microobject 4 and the solid-phase material 10 to an extent in which the immobilization of the microobject 4 and the solid-phase material 10 is not disturbed. This can be achieved by the adjustment of the relationship between the molecular weight of the intermediate agent 20 and the molecular weight of the microobject 4 and also by making smaller the layer thickness during the immobilization of the intermediate agent 20 to the solid-phase material 10 than the diameter of the microobject 4. If the thickness of the immobilized layer of the intermediate agent 20 is sufficiently small as compared with the total length, such as the diameter, of the microobject 4, the immobilization can be secured by an inherent immobilization principle even if the direct contact of the microobject 4 and the solid-phase material 10 is avoided or restrained with the intermediate agent 20. For example, the layer thickness of the immobilized layer of the immobilized intermediate agent 20 is preferably ½ or less of the diameter of the microobject 4. The layer thickness of the immobilized layer of the intermediate agent 20 is more preferably about 1 nm or less.

In this immobilization step, when the solid-phase material 10 is a photoresponsive material and when the inherent immobilization principle is light fixation, the intermediate agent 20 is subjected to light fixation, and further the intermediate agent 20 together with the microobject 4 that interacts therewith can be light-immobilized to the solid-phase material 10. In particular, when light fixation is used by such 2 stages, the orientation of the microobject 4 can be improved by the presence of the intermediate agent 20 as compared with the case where the intermediate agent 20 is not used. Additionally, according to light fixation, though the microobject 4 does not originally need an element for special immobilization, the use of the intermediate agent 20 can also exclude an operation that introduce an element for orientation into the microobject 4. Moreover, this simply permits the orientation of the microobject 4 and also introduction of an element for orientation into the microobject 4 can exclude disadvantages such as decreases in activity and stability of the microobject 4.

The light fixation of the microobject 4 can be executed as in the case of the light fixation of the intermediate agent 20. That is, the microobject 4 may be supplied to the intermediate agent 20 or its vicinity, and then the resulting material may be subjected to light irradiation. In addition, even when the intermediate agent 20 is subjected to light fixation, this intermediate agent 20 can be used to subject the microobject 4 to light fixation. This means that, even when the intermediate agent 20 is made present on the surface of a photoresponsive material, the microobject 4 can be subjected to light fixation via the intermediate agent 20 and/or by superposing the intermediate agent 20 thereon. It was neither conventionally known nor expected at all that the repetition of such light irradiation can subject two or more microobjects (here, corresponding to the intermediate agent 20 and the microobject 4) to light fixation in two or more stages.

As described so far, according to the method of immobilizing the microobject of the present teachings, when the microobject 4 is oriented and immobilized to the solid-phase material 10, the intermediate agent 20 that is made present in the solid-phase material 10 comprises a first element that orients the microobject 4, so that the microobject 4 can be readily oriented and fixed to the solid-phase material 10 while maintaining the activity of the microobject 4 without separately introducing an element for the orientation into the microobject 4. Additionally, a direct interaction for an orientation between the microobject 4 and the solid-phase material 10 is avoided or restrained to be capable of orienting and fixing the microobject 4 to the solid-phase material 10. As a result, the orientation of the microobject 4 to the solid-phase material 10 can reduce the adverse effect on the microobject 4. Moreover, the intermediate agent 20 can also increase the amount of immobilization of the microobject 4.

In addition, the immobilization of the microobject 4 via the intermediate agent 20 directly contact the microobject 4 with the solid-phase material 10, thus restraining or avoiding decreases in activity, storage stability and the like, thereby being capable of immobilization by impartment of orientation with the activity of the microobject 4 being secured. In other words, the surroundings of the activity is not adversely affected (extinction of active sites by immobilization and obstruction of a stereostructure change necessary for function achievement by immobilization) and is immobilized.

Additionally, when the microobject 4 is immobilized by light fixation, the microobject 4 has the possibility of greatly affecting by the solid-phase material 10 because the microobject 4 is immobilized by the light deformation of the solid-phase material 10. However, interposition of the intermediate agent 20 and the resultant oriented immobilization enables the microobject 4 to be immobilized to the solid-phase material 10 with the stability and activity of the microobject 4 being improved.

(Solid Phase Support for Immobilization of Microobject)

The solid phase support of the present teachings can comprise a solid-phase material and an intermediate agent which is immobilized to the surface of the solid-phase material and has a first element that can be at least interactive with a microobject. The solid phase support of the present teachings can be made for the immobilization of a microobject. According to the solid phase support of the present teachings, an intermediate agent makes it possible to orient and fix the microobject and also immobilize the microobject to the solid-phase material with the direct contact of the microobject and the solid-phase material being avoided or restrained. Therefore, the microobject can be oriented and immobilized to the solid-phase material with the stability and activity of the microobject being improved.

In the solid phase support of the present teachings, the solid-phase material is preferably a photoresponsive material. When the solid-phase material 10 is a photoresponsive material, the intermediate agent can be immobilized by light and the microobject 4 can also be immobilized by light. In addition, the photoresponsive material is preferably any of (meth) acrylic polymers comprising an azo dye-containing unit, urethane polymers and urethane-acrylic polymers. Additionally, when the microobject 4 is a polypeptide, the intermediate agent 20 preferably contains a polypeptide. The intermediate agent 20, when being a polypeptide, preferably comprises an α-helix structure, and more preferably in this α-helix structure, 50% or more of the constituent amino acid residue is a hydrophobic amino acid residue. Moreover, the intermediate agent comprises an N-terminus of the α-helix structure or a positive charge connected to the N-terminus. In addition, a polypeptide that is the intermediate agent 20 preferably has an amino acid residue having 12 to 20 residues, both inclusive.

The solid phase support of the present teachings will be described referring to FIG. 2(a). A solid phase support 32 can also comprise, for example, the intermediate agent 20 on the surface of the solid-phase material 10 in dot form as shown in FIG. 2(a) and can also comprise the intermediate agent 20 on the whole surface of the solid-phase material 10 as shown in FIG. 2(b). Additionally, the solid phase support 32 is not limited to a form shown in FIG. 2, and can include all the forms of the forms capable of being taken by the solid-phase material described in the method of immobilizing the microobject of the present teachings and preferred forms. Similarly, the forms which the intermediate agent and the microobject described in the immobilization method of the present teachings may take and preferable forms can all be applied to the intermediate agent 20 and the microobject 4 on the solid phase support 32.

(Method of Manufacturing Solid Phase Support for Immobilization)

The method of manufacturing the solid phase support for immobilization of the present teachings can comprise a preparatory step of preparing a solid-phase material and an intermediate agent immobilization step of immobilizing an intermediate agent having a first element that can be at least interactive with the microobject to the surface of the solid-phase material. According to this manufacturing method, there can be provided a solid phase support that can realize the oriented immobilization and an increase in the amount of the immobilization of an microobject while avoiding or restraining a decrease in activity and the like to the microobject. To the immobilization of a solid-phase material, an intermediate agent, a microobject and an intermediate agent in this manufacturing method can be all applied the solid-phase material in the method of immobilizing the microobject of the present teachings, the intermediate agent and its immobilization and forms that are taken by the microobject and preferred forms.

The manufacturing method of the present teachings can be carried out as, for example, a preparatory step of a solid-phase material (FIG. 1(a)) and a step of immobilizing an intermediate agent (FIG. 1(b)), in the method of immobilizing a microobject of the present teachings. The step of immobilizing an intermediate agent preferably immobilizes an intermediate agent to the surface of a solid-phase material by light irradiation. The light fixation of an intermediate agent and a microobject in two stages can immobilize the microobject 4 to the solid-phase material 10 in further alleviated conditions and in a state effective for activity exhibition.

(Solid-Phase Body to Which Microobject is Immobilized)

The solid phase body of the present teachings can comprise a solid-phase material, an intermediate agent which has a first element that can be at least interactive with a microobject and is immobilized to the surface of the solid-phase material and a microobject immobilized to the solid-phase material via the intermediate agent. According to the solid-phase body of the present teachings, a microobject is oriented and controlled by an intermediate agent and the microobject is immobilized to a solid-phase material through the intermediate agent, whereby the microobject is oriented while the activity, stability and the like of the microobject are secured.

The solid-phase body of the present teachings will be described referring to FIGS. 3(a) and 3(b). A solid-phase body 2 comprises, for example, the intermediate agent 20 on the surface of the solid-phase material 10 in a dot form, as shown in FIG. 3(a), and the microobjects 4 may also be individually immobilized to such the individual intermediate agents 20, or as shown in FIG. 3(b), different microobjects 4 may also be immobilized to the surface of the intermediate agent 20 as a whole immobilized to the surface of the solid-phase material 10.

The solid-phase body of the present teachings is not limited to the form shown in FIG. 3. A solid-phase material, an intermediate agent and its immobilization, forms that can be used aiming at light fixation of the solid-phase materials and preferable forms, in the method of light fixation of the present teachings, can all be applied to the solid-phase material, the intermediate agent and its immobilization and the microobject in the solid-phase body of the present teachings.

In such a solid-phase body, the microobject is preferably a polypeptide. This is because, in polypeptides, the exposure of active-sites for activity exhibition and stereostructure changes for activity exhibition are important and secured only by orientation control. This is also because the activity and stability of polypeptides are greatly influenced also by a solid-phase material.

The solid-phase body 2, to which the microobject 4 is fixed advantageously to the activity, stability and the like, is suitable for analysis and diagnostic use. Moreover, light fixation is suitable for the immobilization of biomaterials and biological materials such as proteins including an antibody, sugar chains, nucleic acids, and cells. Therefore, the solid-phase body 30 of the present teachings is suitable for devices for analysis and diagnosis such as protein, enzyme, antibody chips, sugar chain chips and nucleic acid chips of DNA and the like and cell chips. Moreover, the solid-phase body is also suitable for a bioreactor made by immobilizing an enzyme, a cell, or the like to the solid phase support 2. This is because the solid-phase body is excellent in optical detection characteristics and thus makes it easy to design and control a reactor an also is excellent in the maintenance stability of the microobject 4. Therefore, a highly effective bioreactor, in particular, a microreactor can be fabricated by the solid-phase body.

(Method of Detecting Interaction Between Microobject and Another Component)

A method of detecting an interaction between a microobject and another component comprises a step of supplying another component to a microobject immobilized to a solid-phase body of the present teachings to cause an interaction and a step of detecting the interaction between the other component and the microobject. According to the method of detection of the present teachings, the detection of interaction good in precision, sensitivity, and the like are possible because a microobject is immobilized in a state advantageous for activity such as interaction and the security of stability. The interactions herein include an electrostatic coupling interaction, an ionic bond interaction, a hydrogen bond interaction, a hydrophobic interaction, a hydrophilic interaction, and the like. In addition, the interactions can include, for example, an interaction between a ligand and a receptor for the ligand, an interaction between a protein having a specific amino acid sequence or structure and a substance such as a protein having affinity to the protein, an interaction between an enzyme and a substrate for the enzyme, an interaction between an antigen and an antibody for the antigen, an interaction between a nuclear acid or a modified nuclear acid that has a specific base sequence and a nuclear acid or a modified nucleic acid that has a complementary base sequence for a specific base sequence of the nuclear acid or the modified nucleic acid, and the like. In this method of detection, the microobject 20 is preferably a biomolecular material such as a biomaterial or a biological material and such an interaction is preferably detected with an optical signal.

(Method of Screening Intermediate Agent and Solid-Phase Body for Screening Intermediate Agent)

A method of screening an intermediate agent of the present teachings comprises a step of preparing a solid-phase material to the surface of which test materials of two or more kinds as candidates of intermediate agents having a first element that can interact with a microobject, a microobject immobilization step of immobilizing a predetermined microobject to the solid-phase material in a situation in which the interaction of the two or more kinds of test compounds on the solid-phase material can be caused, and a step of evaluating fixability of the microobject by the two or more kinds of test compounds. According to this screening method, the orientation of a microobject can be controlled to screen a suitable intermediate agent for being immobilized to a solid-phase material.

The test compound to be screened is not especially limited and can comprise a aspect which an intermediate agent described in the immobilization method of the present teachings may take. In other words, the test compound can comprise various embodiments about the first element, the second element, the hydrophobic region, the hydrophilic region, and the like. The test compound is preferably a polypeptide. When the test compound is made a polypeptide, the test compound can be designed on the basis of various forms described above, about the molecular weight (5000 or less); the number of amino acid residues; the presence or absence of the hydrophobic region (preferably, the C-terminal region); the molecular weight of the hydrophobic region in terms of amino acid residue (700 or more) and the number of amino acid residues, the presence or absence of the helix structure and its amino acid residue composition; and the presence or absence of the electrostatic interaction site (preferably, a positive electric charge and preferably the N-terminal region, and more preferably the N-terminus) and the amino acid residue composition of the electrostatic action site. Specifically, the amino acid residue composition of the polypeptide (sequence) is determined. For the determination of the amino acid sequence, a program is used that instructs an algorithm that searches for an amino acid sequence that fulfills part or the whole of the above requirements and a computer is preferably made to execute this program. In addition, in two or more kinds of test compounds, their structures and compositions are preferably selected in consideration of the characteristics of a microobject that is to be immobilized.

Such an algorithm can comprise, for example, a step of acquiring requirement information concerning the molecular weight and the like of a polypeptide that become search requirements and a step of creating an amino acid sequence that fulfills these requirements on the basis of the acquired requirement information. The step of acquiring requirement information is a step of acquiring requirement information by a computer, i.e., CPU, by selecting various requirements arbitrarily or from a preset range and inputting them from a keyboard or the like by an operator. Hence, the step of acquiring requirement information may include a step of displaying an inquiry screen of various requirements on a display or the like. A part of requirements may be fixed in advance.

The step of creating an amino acid is a step of creating an amino acid sequence by CPU on the basis of acquired requirement information. A specific algorithm that creates an amino acid sequence is not particularly limited to, but can make use of an algorithm or a program such as a well-known Insight II, Accelrys Software Inc. Additionally, when an amino acid sequence is created, information on the easiness of the formation of a helix structure and the properties of various amino acids (hydrophobicity, hydrophilicity, acidity, basicity, and the like) are preferably utilized in addition to the requirement information that describes above. A test compound made of such a polypeptide can be prepared by acquisition by combinatorial chemistry.

In this screening method, a solid-phase material is preferably a photoresponsive material, and a test compound is preferably immobilized to the solid-phase material by light fixation. In this manner, an intermediate agent that is appropriate for two-stage fixation of a microobject (fixation of an intermediate agent and fixation of a microobject) by light fixation can be screened from test compounds.

Various embodiments that may be taken in the immobilization of an intermediate agent and a microobject in the method of immobilization of the present teachings described above can be applied to the step of immobilizing test compounds and given microobjects. Moreover, microobjects to be immobilized may also be one kind or two kinds or more.

To evaluate the fixability of a microobject by a test compound, the amount of immobilization of a microobject can be preferably evaluated in advance. For example, a signal generating element such as an optical signal is imparted in advance to a microobject, and this signal can be detected. For example, a microobject may be labeled with a fluorescent dye such as Cy3 or Cy5 in advance. In addition, when no signaling generating element is imparted to a microobject, the amount of immobilization of an immobilized microobject can be evaluated using a labeled antibody that recognizes the microobject and also a microobject can also be quantitatively detected by some reaction, color reaction, luminous reaction, or the like.

In the step of evaluating the fixability of this screening method, the fixability of a microobject with orientation control by a test compound can be evaluated. For this, a component that reacts only with a specific portion of a microobject to be immobilized is supplied to an immobilized microobject and then the amount of its reaction product may simply be detected. The evaluation of fixability with orientation control can use the evaluation of the activity of an immobilized microobject (function). For example, an antibody is used as a microobject and a labeled compound such as a labeled antibody or a labeled enzyme that is recognized and captured as a reaction component by the antigen-recognition site of an antibody can be used. Additionally, an enzyme is used as a microobject, the substrate or coenzyme of this enzyme is used as a reaction component and the reaction product may be quantitatively detected.

Moreover, a solid-phase body comprising a solid-phase material, test compounds of two or more kinds, preferably 10 or more kinds, as candidates of intermediate agents that are immobilized to the surface of a solid-phase material and have a first element that can be interactive with a microobject can be utilized as a solid-phase body for screening for an intermediate agent for the immobilization of a given microobject. This solid-phase body for screening preferably comprises a substrate-shaped solid-phase material so as to be efficiently appreciable by seeing the fixability of an intermediate agent all at once and more preferably comprises test compounds in an array form. More preferably, the solid-phase material is a photoresponsive material, and test compounds and/or a microobject is immobilized to a solid-phase material by light fixation. Various aspects and preferred embodiments that have disclosed the method of immobilizing a microobject of the present teachings and an optical solid phase support for light fixation of the present teachings can be directly applied to a solid-phase material that can be utilized to a solid-phase body for such screening and a polypeptide as well as the method of manufacturing a solid-phase body.

(Method of Screening Microobject and Solid-Phase Body for Screening Microobject)

A method of screening a microobject of the present teachings comprises a step of preparing a solid-phase material to the surface of which is immobilized a predetermined intermediate agent having a first element that can interact with the microobject, a microobject immobilization step of immobilizing two or more kinds of test compounds as candidates of the microobjects onto the solid-phase material in a situation in which the interaction of the intermediate agent on the solid-phase material can be caused, and a step of evaluating fixability and/or orientation of the two or more kinds of test compounds. According to this screening method, a microobject suitable for being immobilized to a solid-phase material by making use of a given intermediate agent to control the orientation can be screened from a test compound.

The test compound to be screened is not especially limited and can comprise a aspect which a microobject described in the immobilization method of the present teachings may take. The test compound is preferably a polypeptide. In addition, a test compound selected by the method of screening an intermediate agent can be used as a given intermediate agent in addition to an intermediate agent described by the immobilization method of the present teachings.

Additionally, also in the screening method of the present teachings, a solid-phase material is preferably a photoresponsive material, and a test compound is preferably immobilized to the solid-phase material by light fixation. In this manner, a microobject that is appropriate for two-stage fixation of a microobject (fixation of an intermediate agent and fixation of a microobject) by light fixation can be screened from test compounds.

Various embodiments that may be taken in the immobilization of an intermediate agent and a microobject in the method of immobilization of the present teachings described above can be applied to the steps of immobilizing a predetermined intermediate agent and test compounds. Moreover, a predetermined intermediate agent to be immobilized may also be one kind or two kinds or more.

A method similar to the method described in the method of screening an intermediate agent can be adopted to evaluate the amount of immobilization and the orientation of a microobject. That is, a signal generating element can be imparted in advance to a test compound that is the screening target.

In addition, a solid phase support comprising a solid-phase material and a given intermediate agent that is immobilized to the surface of the solid-phase material and has the first element that can be interactive with the microobject can be utilized as a solid-phase body for screening for a microobject. This solid-phase body for screening also preferably comprises a substrate-shaped solid-phase material similar to a solid-phase body for screening an intermediate agent and more preferably comprises a predetermined intermediate agent in an array form. More preferably, the solid-phase material is a photoresponsive material, and test compounds and/or a microobject is immobilized to a solid-phase material by light fixation. Various aspects and preferred embodiments that have disclosed the method of immobilizing a microobject of the present teachings and an optical solid phase support for light fixation of the present teachings can be directly applied to a solid-phase material that can be utilized to a solid-phase body for such screening and a polypeptide as well as the method of manufacturing a solid-phase body.

Some of the aforementioned characteristics of the present teachings are described below.

According to the present teachings, a solid phase support for immobilizing a microobject is provided. The solid phase support may comprise a solid-phase material and an intermediate agent that is immobilized to the surface of the solid-phase material and described above. In this solid phase support, the solid-phase material may be made a photoresponsive material that contains a photoresponsive component that deforms by light irradiation, and the photoresponsive material may be selected from (meth)acrylic polymers, urethane polymers and urethane-acrylic polymers, comprising an azo dye-containing unit.

According to the present teachings, a method of producing a solid phase support for immobilization to immobilize a microobject may be provided. The method comprises a preparatory step of preparing a solid-phase material, and an intermediate-agent immobilization step of immobilizing an intermediate agent described in any of the above to the surface of the solid-phase material.

According to the present teachings, a method of detecting an interaction between a microobject and another component may be provided. The method comprises a step of supplying the other component to the microobject that is placed on a solid-phase body as described in above to cause the interaction, and a step of detecting the interaction between the other component and the microobject.

According to the present teachings, a method of screening an intermediate agent to immobilize a microobject to a solid-phase material may be provided. The method comprises: a step of preparing a solid-phase material, to which test materials of two or more kinds as candidates of intermediate agents, each intermediate agent having a first element that is capable of interacting with the microobject, are immobilized on the surface thereof, a microobject immobilization step of immobilizing a predetermined microobject to the solid-phase material in a situation in which the interaction of the two or more kinds of test compounds on the solid-phase material can be exhibited, and a step of evaluating fixability of the microobject by the two or more kinds of test compounds. In addition, according to the present invention, a solid phase support for screening of an intermediate agent to immobilize a microobject to a solid-phase material may also be provided. The support comprises a solid-phase material and two or more kinds of test compounds as candidates, and of which are immobilized to the surface of the solid-phase material, and of which have first elements that can interact with the microobject.

According to the present teachings, a method of screening a microobject may be provided. The method comprises a step of preparing a solid-phase material to the surface of which a predetermined intermediate agent having a first element that can interact with the microobject, a microobject immobilization step of immobilizing two or more kinds of test compounds as candidates of the microobjects onto the solid-phase material in a situation in which the interaction of the intermediate agent on the solid-phase material can be caused, and a step of evaluating fixability and/or orientation by the two or more kinds of test compounds. In addition, according to the present teachings, also a solid phase support that is a solid phase support for screening of a microobject may be provided. The support comprises a solid-phase material, and a predetermined intermediate agent that is immobilized to the surface of the solid-phase material and has a first element that can interact with the microobject.

Hereinafter, the present teachings will be described by way of specific examples; however, the present teachings is by no means limited to the following examples.

Example 1

Design of Intermediate Molecule

Synthetic Peptide

A number of α helix peptides of 20 residues (SEQ ID NO: 46-101) shown in FIG. 4 were designed as an intermediate molecule, and a peptide library was synthesized chemically. These peptides, when forming α helix as shown in FIG. 5(a), have a hydrophobic amino acid residue predominantly arranged at least on one side of the α helix in a spiral dorection and exhibite hydrophobicity at least on the side. In other words, as shown in FIG. 5(b), a wheel model in which an α helix structure of two rotations is taken as a wheel was constructed and hydrophobic amino acid residues were coordinated to a, b, e and f positions of an amino acid sequence (a, b, c, d, e, f, g) along the rotation direction of the α helix. Additionally, these synthetic peptides all had 20 or less amino acid residues and had a molecular weight of 5000 or less (700 to 2200).

Example 2

Evaluation of Fixability

1 μL each of a 100 μg/mL aqueous solution of each synthetic peptide was added dropwise to an AZO film, vacuum-dried and was subjected to light irradiation (20 mW/cm$^2$) at 25° C. for 0.5 hour. Thereafter, the resulting material was washed with TPBS three times and the synthetic peptide was subjected to light fixation. To this was added dropwise 50 μL of a 1 μg/mL Cy5-labeled Goat anti mouse IgG (AP127S, available from CHEMICON International Inc.)/TPBS solution and the resulting material was irradiated with light (20 mW/cm$^2$) at 25° C. for 17 hours to light-fix the antibody, with the material covered with a gap cover glass plate. Thereafter, the resulting material was washed with TPBS 3 times for 1 minute. This slide glass was set in an array scanner and the amount of fluorescence of the spot made by adding dropwise the peptide was determined. The results are shown in FIG. 6.

Figure 6:
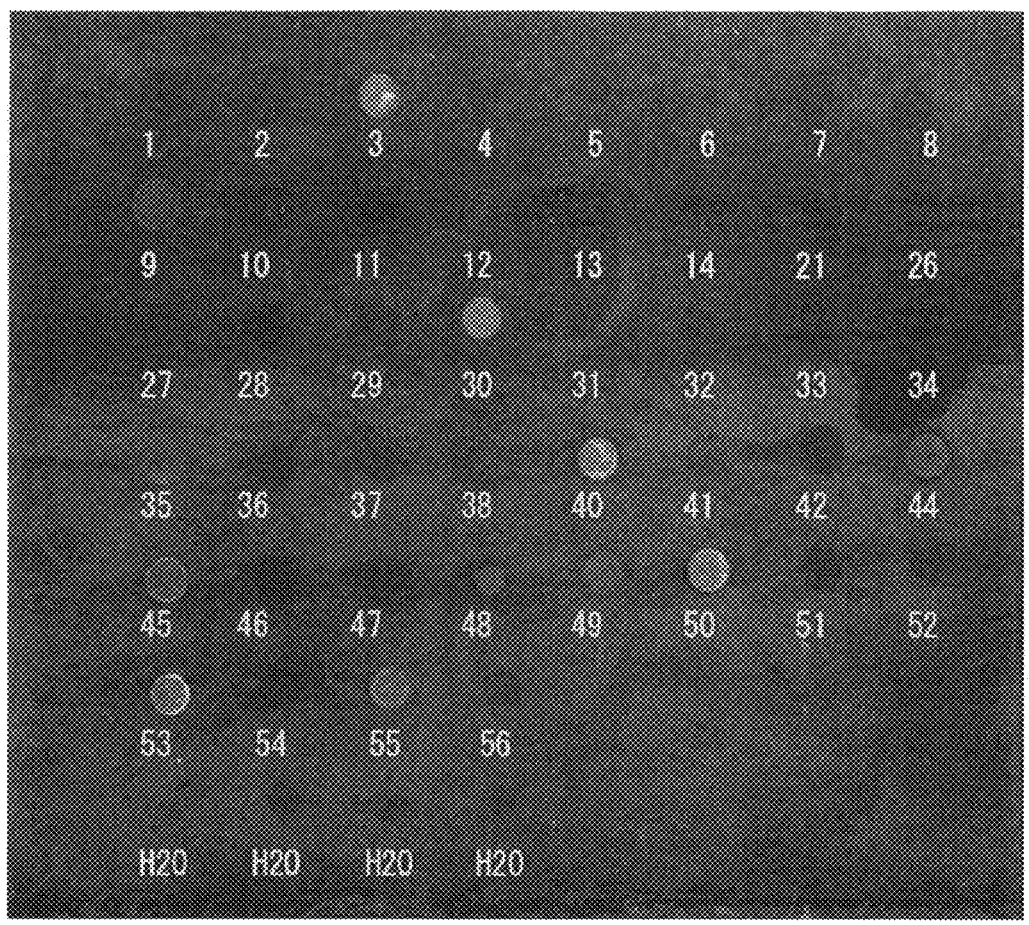
FIG. 6 shows a result of evaluation of the antibody immobilization capability in Example 2.

As shown in FIG. 6, the fluorescence intensities of several spots of the spots (1 to 56) were significantly high as compared with the fluorescence intensity of the region where a peptide was not immobilized. This supports that a synthetic peptide that is an intermediate molecule has an affinity for an antibody in a solution and can make the antibody adsorbed on the surface of an AZO film.

Moreover, the AZO film used in this example and the following examples used an azo polymer (m:n=15:85) shown in the following formula. 200 mg of this azo polymer was dissolved in 16 ml of a pyridine solution. Thereafter, this solution was filtered with a filter of 0.22 μm. A slide glass wiped by acetone impregnated cotton was dried and then 80 μl of the polymer solution was added dropwise thereto using a spin cast machine. The material was spined for 10 seconds at 4000 rpm/sec, dried at 60° C. for 2 hours and then the AZO film was fabricated by vacuum-drying the resulting material under shading at 60° C. for 2 hours.

[Formula 2]

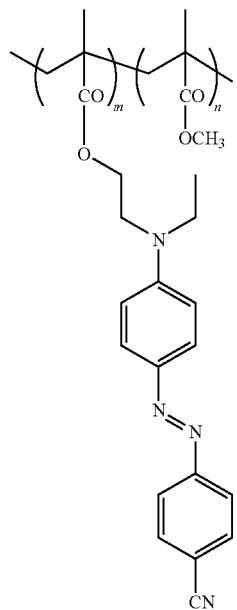

formula 2 m:n = 15:85

Example 3

Evaluation of Effect of Light Irradiation

The difference of the amounts of light fixation with and without light irradiation (25° C. for 17 hours) in the experimental procedure of Example 2 was evaluated. Results are depicted in FIG. 7.

Figure 7:
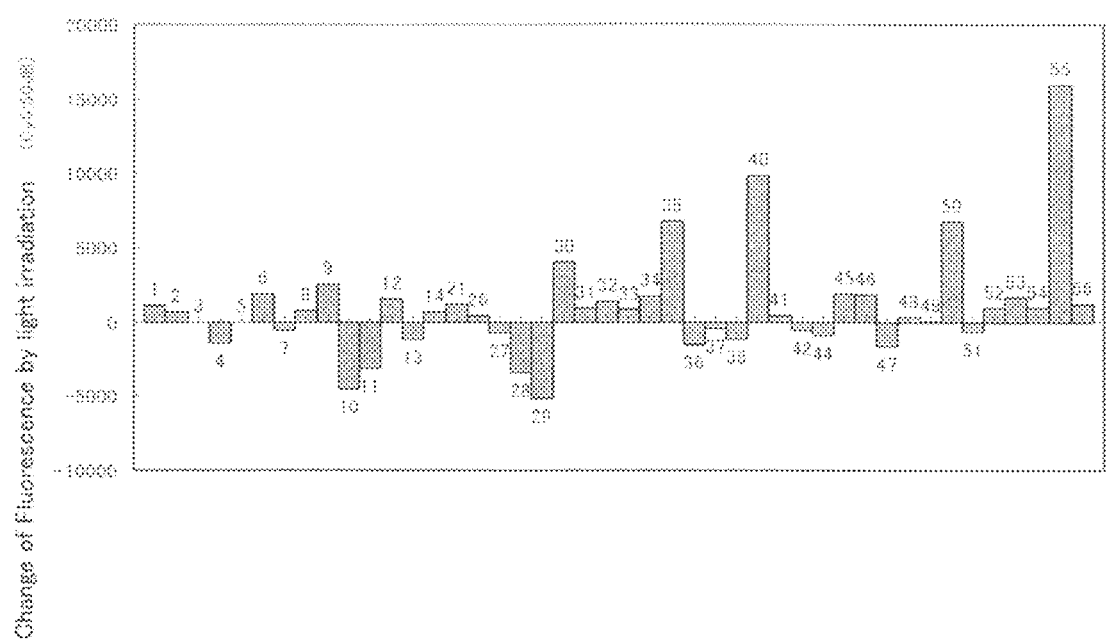
FIG. 7 shows a result of evaluation of a light irradiation effect in Example 3. An increase in the fluorescent amount shows that the amount of antibody immobilization is increased by repeated light irradiation and this increase in the amount of the antibody immobilization strongly supports a result caused by light irradiation.

As shown in FIG. 7, the amounts of fluorescence were increased in a plurality of peptides (Nos. 1, 2, 6, 8, 9, 12, 14, 21, 30, 31, 32, 33, 34, 35, 40, 41, 45, 46, 50, 52, 53, 54, 55, and 56) by light irradiation in the presence of an antibody. This strongly supports that AZO films have an action of immobilizing an antibody even in a state in which a synthetic peptide that is an intermediate molecule is used. The maintenance of fixability in the presence of an intermediate agent by light irradiation relates to the fact that the immobilization principle of light fixation is due to surface deformation and a microobject is thought to be directly interactive with a support.

Example 4

Figure 8:
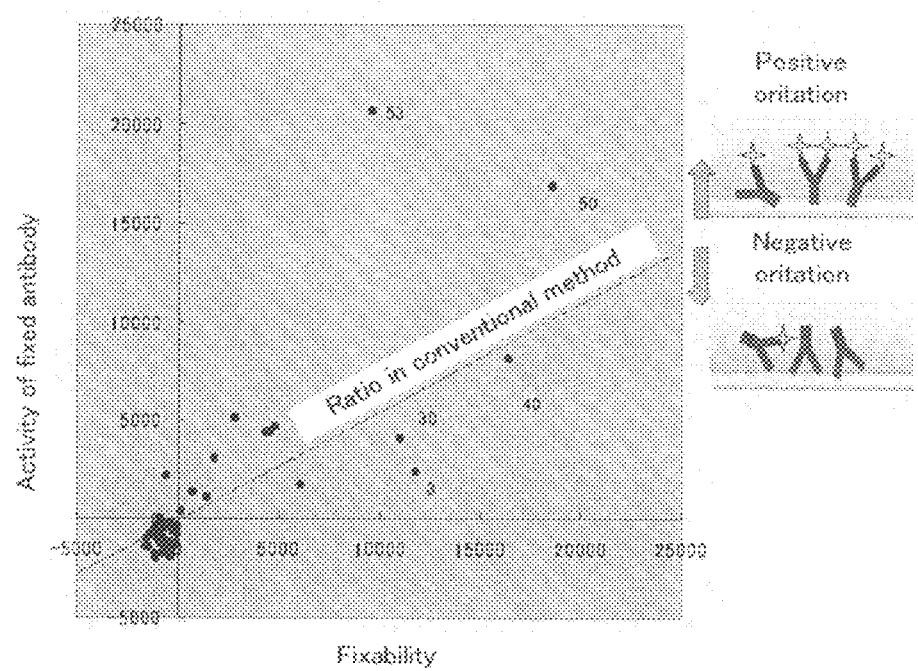
FIG. 8 shows an evaluation result of the orientation control of an antibody by a synthetic peptide in Example 4.

Evaluation of Immobilized Antibody and Orientation when α Helix Peptide of 20 Residues is Used (1) Evaluation of Immobilized Antibody A synthetic peptide was coated on the AZO film by a method as described in Example 2. To this was added dropwise 50 μL of a 1 Mg/mL of anti goat IgG rabbit-IgG (A50-100A, available from Bethyl Laboratories, Inc.)/TPBS solution and the resulting material was irradiated with light (20 mW/cm$^2$) at 25° C. for 17 hours to light-fix the antibody. Thereafter, the resulting material was washed with TPBS 3 times for 1 minute. To this was added dropwise 50 μL of a 1 μg/mL Cy5-labeled Goat anti Mouse IgG (AP127S, available from CHEMICON International Inc.)/TPBS solution and the resulting materials were reacted for 30 minutes at 25° C. Thereafter, the resulting material was washed with TPBS 3 times for 1 minute. This slide glass was set in an array scanner and the amount of fluorescence of the spot made by adding dropwise the peptide was determined to evaluate the immobilization ability of the antibody. FIG. 8 shows the relationship between the fixability (Example 2) and the immobilization ability of the antibody evaluated by this example, for each peptide. FIG. 8 also shows the case where an antibody solution was added dropwise to an AZO film and dried and then subjected to light fixation (conventional method).

It is considered that, as shown in FIG. 8, peptides with high immobilization ability of antibodies (peptide Nos. 50 and 53) have an active site of the antibody that tends to direct the solution, which improves the orientation of the antibody, as compared with the case where an antibody solution is added dropwise to an AZO film, dried and then light-fixed (conventional method). On the other hand, it is considered that, in the peptides having low immobilization ability of antibodies (peptide Nos. 3, 30, and 40) to fixation capacity, the active site of the antibody is oriented to the AZO film. This supports that the two-stage fixation method can control the orientation of an immobilized antibody.

Example 5

Immobilization Ability of Antibodies and Orientation when N-Terminal Recognition Peptide is Used 1 µL each of a 100 µg/mL aqueous solution of each synthetic peptide (FIG. 9) was added dropwise to an AZO film, vacuum-dried and was subjected to light irradiation (20 mW/cm$^2$) at 25° C. for 0.5 hour. Thereafter, the resulting material was washed with TPBS three times for 5 minutes and the synthetic peptide was immobilized. 1 µL of a 0 to 400 ng/mL of Rabbit anti Goat IgG/TPBS solution was added dropwise to each position to which was added dropwise a peptide and which was immobilized. The resulting material was incubated for 17 hours while subjecting to light irradiation (20 mW/cm$^2$) at 25° C. Thereafter, the resulting material was washed with TPBS 3 times for 1 minute.
(Evaluation of Fixability)
A 1 µg/mL Cy5-labeled Mouse anti Rabbit IgG (AP188S)/TPBS solution was added dropwise to an AZO film to which a peptide was immobilized, the resulting materials were reacted at 25° C. for 30 minutes and then was washed with TPBS for 1 minute 3 times. This slide glass was set in an array scanner, the amount of fluorescence of the Cy5 was determined and the amount of fluorescence of the spot made by adding dropwise the peptide was quantitated.
(Evaluation of Immobilization Ability of Antibody)
In addition, a 1 µg/mL Cy5-labeled Mouse anti Goat IgG (AP127S)/TPBS solution was added dropwise to top of a peptide on an AZO film to which the peptide was immobilized, the resulting materials were reacted at 25° C. for 30 minutes and then was washed with TPBS for 1 minute 3 times. This slide glass was set in an array scanner, the amount of fluorescence of the Cy5 was determined and the amount of fluorescence of the spot made by adding dropwise the peptide was quantitated.
Additionally, the conventional method has a step of adding dropwise a synthetic peptide that involves adding dropwise 1 µL of 0 to 400 ng/mL of Rabbit anti Goat IgG/TPBS solutions in place of a synthetic peptide and subjecting the material to light fixation.

The orientation was evaluated based a index that is a ratio of the immobilized antibody activity to fixability and values were calculated as a ratio when the index of conventional method was regarded 1. The results are presented in FIG. 9.

Figure 9:
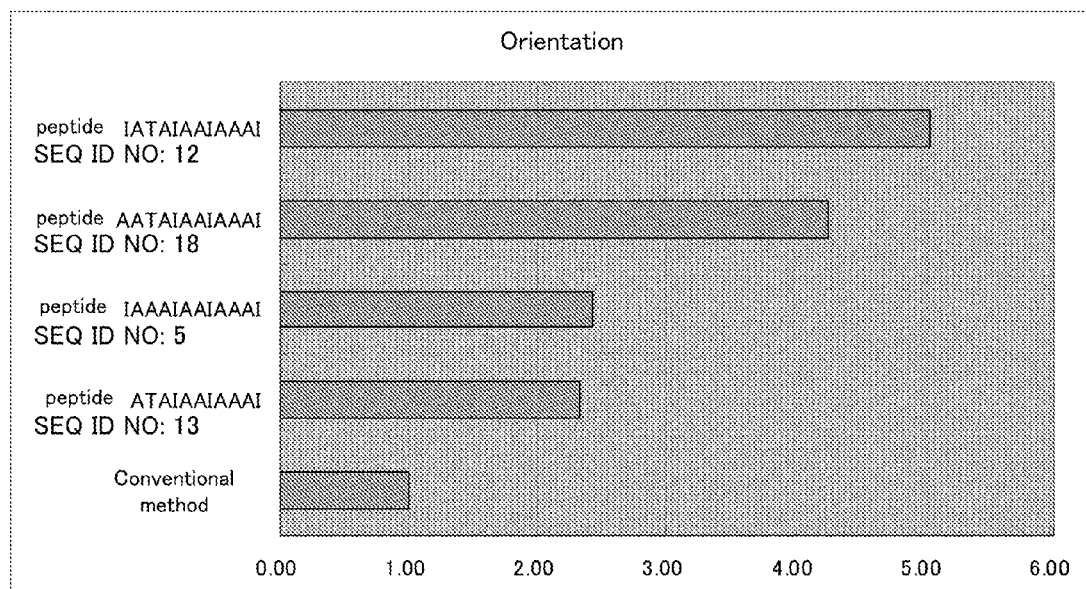
FIG. 9 shows the amino acid sequence and an orientation evaluation result of a synthetic peptide used in Example 5.

As shown in FIG. 9, the light fixation of a peptide in two stages led to obtaining a high value of 2.3 to 5 times the value obtained by the conventional method. This supports that the two-stage fixation method can possibly control the orientation of an immobilized antibody. Moreover, it also supports that the protective action on an antibody produced by use of a peptide.

Example 6

50 µL of a stock solution of a StabilGuard Biomolecule Stabilizer (SG01-0125, SurModics Co.) was added dropwise to an AZO film and the resulting material were reacted for 30 minutes at room temperature and then the reactant was washed with TPBS for 1 minute three times. It is estimated that this treatment makes the surface of the AZO film hydrophilic to thereby coat the polymer component (not containing a protein component).
(Evaluation of Fixability)
1 µL of a 100 to 500 ng/mL Cy5-labeled Mouse anti Goat IgG (A P127S)/TPBS solution was added dropwise to top of the polymer component on a substrate and this was vacuum-dried and then was irradiated with light (20 mW/cm$^2$) at 25° C. for 0.5 hour. Thereafter, this was immersed in a TPBS solution and shaken for 5 minutes to thereby clean the material. A 1 µg/mL Cy5-labeled Mouse anti Goat IgG (AP127S)/TPBS solution was added dropwise thereto, the resulting materials were reacted at 25° C. for 30 minutes and then was washed with TPBS for 1 minute 3 times. This slide glass was set in an array scanner and the amount of fluorescence of the Cy5 was determined.
(Evaluation of Immobilization Ability of Antibodies)
In addition, similarly, 1 µL of a 0 to 400 ng/mL Rabbit anti goat IgG (A50-100A)/TPBS solution was added dropwise to a substrate and this was vacuum-dried. Thereafter, this was immersed in a TPBS solution and shaken for 5 minutes to thereby clean the material. A 1 µg/mL Cy5-labeled Mouse anti Goat IgG (AP127S)/TPBS solution was added dropwise thereto, the resulting materials were reacted at 25° C. for 30 minutes and then was washed with TPBS for 1 minute 3 times. This slide glass was set in an array scanner and the amount of fluorescence of the Cy5 was determined.

The slope was calculated from the fluorescence intensity of the spot and the dropwise addition concentration of the antibody solution. FIG. 10 shows the results when a StabilGuard Biomolecule Stabilizer was treated and not treated.

As shown in FIG. 10, an antibody has been shown to be immobilized even after coating. Additionally, the amount of immobilization was reduced by half; however, the orientation was improved. As described above, even if the intermediate agent is an organic polymer other than a peptide, the orientation of a microobject was shown to be capable of being controlled.

Example 7

Evaluation of Hydrophobic Helix Structure (Evaluation of Peptide Fixation Amount)
Various synthetic peptides shown in FIG. 11 were fixed on an AZO film by a method similar to Example 2. After immobilization, 50µ of a 1 µg/mL Cy5 mono-reactive-dye (PA25001, GE Healthcare)/PBS solution was added dropwise thereto and the materials were reacted at room temperature for 30 minutes. Thereafter, the resulting material was washed with TPBS for 1 minute 3 times and this slide glass was set in an array scanner and the amount of fluorescence of the spot made by adding dropwise the peptide was determined.

(Evaluation of Fixability)

50 μL of a 1 μg/mL Cy5-labeled Goat anti mouse IgG/TPBS solution was added dropwise to the slide glass after the synthetic peptide was coated and this was subjected to light irradiation (20 mW/cm$^2$) at 25° C. for 17 hours [immobilization of the antibody]. Thereafter, the resulting material was washed with TPBS 3 times for 1 minute. This slide glass was set in an array scanner and the amount of fluorescence of the spot made by adding dropwise the peptide was determined.

Figure 12:
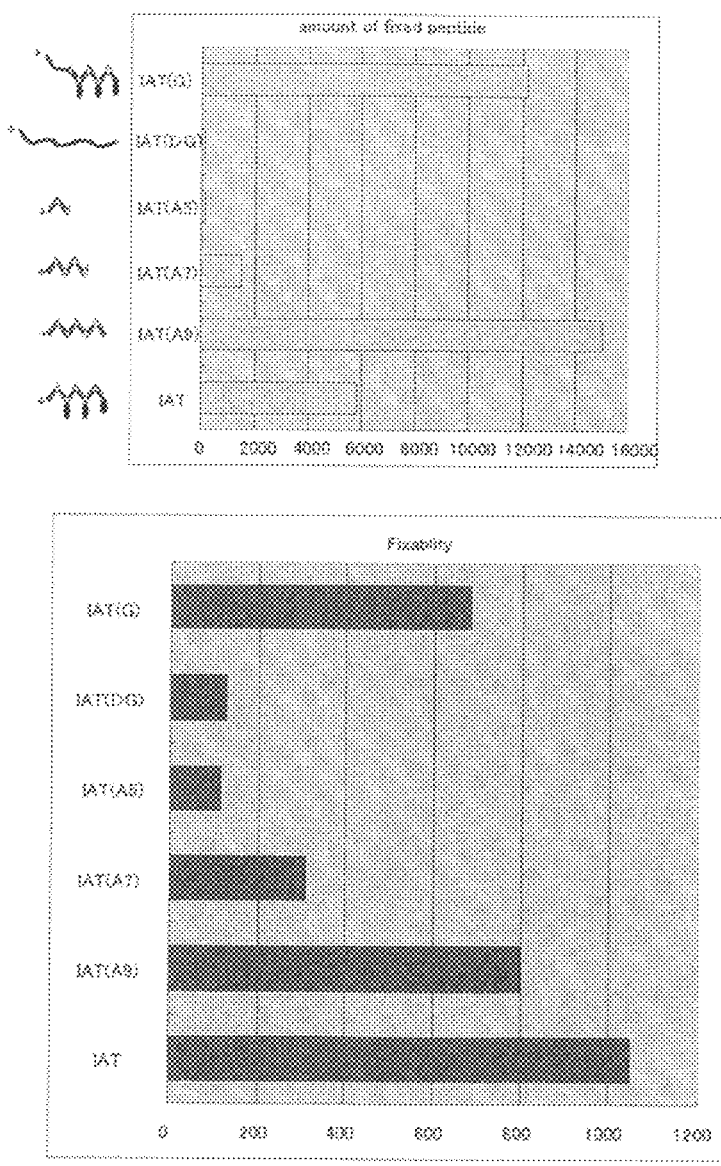
FIG. 12 shows results of evaluation of synthetic peptides in Example 7. The upper diagram indicates amounts of peptide fixation and the lower diagram indicates antibody immobilization capabilities. On the left side of the peptide names of the upper diagram are schematically illustrated stereostructures of the peptides.

FIG. 12 shows the results of evaluating these peptide. FIG. 12 has shown that the peptides IAT, IAT(A9) and IAT(G) immobilize on the AZO film. On the other hand, the peptides IAT(A7), IAT(A5) and IAT(I>G) were shown not to immobilize on the AZO film. The peptides IAT, IAT(A9) and IAT(G) are ascertained to form almost a 100% helix structure by the CD spectral measurement. FIG. 12 shows schematic peptide structures on the left side of the peptide names. Zigzags of peptide structures shown in FIG. 12 indicate an α-helix structure, and the ellipsoidal bodies that direct downward from the zigzag structures of the peptide denotations of IAT(G) and IAT represent hydrophobic groups of isoleucines. As a result, it has been understood that a hydrophobic region, in particular, a hydrophobic helix structure is important in the immobilization of a peptide as an intermediate agent. In addition, the result of fixability depends on the amount of peptide fixation, and therefore the evaluation of a peptide by the Cy5 mono-reactive-dye is considered to well reflect an actual amount of immobilization.

Example 8

(1) Evaluation of Antibody-Immobilization Capability of Synthetic Peptide

1 μL each of a 100 μg/mL synthetic peptide, shown in FIG. 13, was added dropwise to an AZO film, vacuum-dried and was subjected to light irradiation (20 mW/cm$^2$) at 25° C. for 2 hours. Thereafter, the resulting material was washed with TPBS three times for 5 minutes and the synthetic peptide was subjected to light fixation. A 1 μg/mL Cy5-labeled Goat anti mouse IgG/TPBS solution was added dropwise thereto and this was incubated while subjecting to light irradiation (20 mW/cm$^2$) at 25° C. for 17 hours. Thereafter, the resulting material was washed with TPBS three times for 1 minute and the antibody was subjected to light fixation. This slide glass was set in an array scanner, the amount of fluorescence of the Cy5 was determined and the amount of fluorescence of the spot made by adding dropwise the peptide was quantitated. FIG. 13 shows the results.

(2) Evaluation of Immobilized Antibody Activity (1) Various synthetic peptides shown in FIG. 13 by a method similar to the case of the evaluation of the antibody-immobilization capability of a synthetic peptide were subjected to light fixation. A 1 μg/mL Rabbit anti goat IgG/TPBS solution was added dropwise thereto and this was incubated while subjecting to light irradiation (20 mW/cm$^2$) at 25° C. for 17 hours. Thereafter, the resulting material was washed with TPBS three times for 1 minute and the antibody was immobilized. A 1 μg/mL Cy5-labeled Goat anti mouse IgG/ TPBS solution was added dropwise thereto, the resulting materials were reacted at 25° C. for 30 minutes and then the resulting material was washed with TPBS for 1 minute 3 times. This slide glass was set in an array scanner, the amount of fluorescence of the Cy5 was determined and the amount of fluorescence of the spot made by adding dropwise the peptide was quantitated. FIG. 13 shows the results.

Additionally, as Comparative Example 1, water was added dropwise in (1) instead of the synthetic peptide solution. As Comparative Example 2, a 10 μg/mL Rabbit anti goat IgG/TPBS solution was added dropwise in (2) instead of the synthetic peptide solution. As Comparative Example 3, the sequence EATAIAAIAAAI was used as a synthetic peptide in (1) and (2). As Comparative Example 4, the sequence EAAA-IAAIAAAI was used as a synthetic peptide in (1) and (2).

Moreover, the orientation of each synthetic peptide was calculated by using the ratio of the immobilized antibody activity obtained in (2) to the fixability obtained in (1) and by setting to be 1 the ratio of the immobilized antibody activity to the fixability in the case where a 10 μg/mL Rabbit anti goat IgG was dried and light-fixed in Comparative Example 2. FIG. 13 shows the results as well.

As shown in FIG. 13, the fixabilities of the synthetic peptides 1 to 33 were increased by a factor of 10 or more as compared with the case of Comparative Example 1. This seems to be because the peptides listed in FIG. 13 markedly improved the adsorpability of the antibodies. On the other hand, the fixability decreased remarkably in Comparative Examples 3 and 4. This indicates that the amino group of the N-terminus interacts with the molecular surface of the antibody and this phenomenon seems to be because the carboxyl group of the glutamic acid (E) located in the N-terminus inhibits the interaction of the amino group of the N-terminus and the antibody molecule.

The activity of an antibody that was adsorbed on a support through a synthetic peptide (immobilized antibody activity) was increased by a factor of 3 to 30 as compared with the case of an antibody directly subjected to light fixation (Comparative Example 2). The value indicating the activity for each immobilized antibody (orientation) was 3 to 6 times the case of an antibody directly subjected to light fixation (Comparative Example 2). This supports that (1) the antigen-recognition site of an immobilized antibody is not interactive with a support (or a peptide) and is oriented to the aqueous solution and that (2) an antibody keeps an original stereostructure as compared with a directly immobilized case.

The amino acid sequence of the three residues on the N-terminal side of the synthetic peptides 1 to 33 screened on the basis of the fixability and orientation as indexes has shown that the amino group of the N-terminus is important not to be modified and that threonine or serine is included within the three residues on the N-terminal side.

In addition, it has been shown that the combinations of three residues on the N-terminal side having high immobilization ability of antibodies and an orientation of 3 times or more include IAA, VAA, FAA, PAA, AAA, LAA, QAA, IAT, ATA, FAT, WAT, VAT, LAT, AAT, PAT, IHT, IPT, IIT, IMT, IST, ITT, IQT, IAS, IGS, IVS, ISS, ITS, IQS, INS, IAY, IAE, and IAI. It has been shown that, of these, the combinations of three residues on the N-terminal side having an orientation of 5 times or more include IAT, ITT, ITS and IAS, and the combinations of three residues on the N-terminus having particularly high immobilization ability of antibodies and an orientation of 3 times or more include IPT, IMT, IST, IQT, IQS and INS.

What is claimed is:

1. A method of orienting and immobilizing a microobject on a surface of a photo-responsive material, the method comprising:
    applying an intermediate agent having a molecular weight of 5000 or less to the surface of the photo-responsive material;
    applying the microobject to the surface of the photo-responsive material;
    orienting the microobject through non-covalent interaction with the intermediate agent at the surface of the photo-responsive material; and
    light-irradiating the photo-responsive material to deform the surface of the photo-responsive material and to non-covalently immobilize the microobject,
    wherein the intermediate agent is immobilized on the surface of the photo-responsive material.

2. The method of claim 1, the method further comprising light-irradiating the photo-responsive material to deform the surface of the photo-responsive material and to non-covalently immobilize the intermediate agent before applying the microobject.

3. The method of claim 1, wherein the microobject is oriented through electrostatic interaction or hydrophilic interaction with the intermediate agent.

4. The method of claim 1, wherein the intermediate agent comprises a hydrophobic portion that is drawn to the surface of the photo-responsive material when the intermediate agent is applied to the surface of the photo-responsive material.

5. A method of orienting and immobilizing a biomolecule on a surface of a photo-responsive material, the method comprising:
    applying an intermediate agent having a molecular weight of 5000 or less to the surface of the photo-responsive material;
    applying the biomolecule to the surface of the photo-responsive material;
    orienting the biomolecule through non-covalent interaction with the intermediate agent at the surface of the photo-responsive material; and
    light-irradiating the photo-responsive material to deform the surface of the photo-responsive material and to non-covalently immobilize the biomolecule,
    wherein the intermediate agent is immobilized on the surface of the photo-responsive material.

6. The method of claim 5, the method further comprising light-irradiating the photo-responsive material to deform the surface of the photo-responsive material and to non-covalently immobilize the intermediate agent before applying the biomolecule.

7. The method of claim 5, wherein the biomolecule is oriented through electrostatic interaction or hydrophilic interaction with the intermediate agent.

8. The method of claim 5, wherein the intermediate agent comprises a polypeptide chain.

9. The method of claim 8, wherein the polypeptide chain comprises amino acid residues in an α-helix.

10. The method of claim 9, wherein 50% or more of the amino acid residues are hydrophobic.

11. The method of claim 10, wherein 8 or more consecutive amino acid residues are hydrophobic.

12. A method of orienting and immobilizing a first polypeptide on a surface of a photo-responsive material, the method comprising:
applying a second polypeptide to the surface of the photo-responsive material, the second polypeptide having a molecular weight that is 5000 or less and less than a molecular weight of the first polypeptide;
applying the first polypeptide to the surface of the photo-responsive material;
orienting the first polypeptide through non-covalent interaction with the second polypeptide at the surface of the photo-responsive material; and
light-irradiating the photo-responsive material to deform the surface of the photo-responsive material and to non-covalently immobilize the first polypeptide,
wherein the second polypeptide is immobilized on the surface of the photo-responsive material.

13. The method of claim 12, the method further comprising light-irradiating the photo-responsive material to deform the surface of the photo-responsive material and to non-covalently immobilize the second polypeptide before applying the first polypeptide.

14. The method of claim 12, wherein the first polypeptide is a protein.

15. The method of claim 14, wherein the protein is an antibody.

16. The method of claim 12, wherein the second polypeptide comprises amino acid residues in an α-helix.

17. The method of claim 16, wherein 50% or more of the amino acid residues are hydrophobic.

18. The method of claim 17, wherein 8 or more consecutive amino acid residues are hydrophobic.

19. The method of claim 17, wherein the hydrophobic amino acid residues are alanine or isoleucine.

20. The method of claim 16, wherein the amino acid sequence of the α-helix is selected from the group consisting of SEQ ID Nos.: 1-4.

21. The method of claim 12, wherein the second polypeptide has a non-acidic amino acid residue at an N-terminal.

22. The method of claim 21, wherein the second polypeptide has serine or threonine at the second or third position from the N-terminal.

23. The method of 12, wherein the second polypeptide has an N-terminal selected from the group consisting of IAA, VAA, FAA, PAA, AAA, LAA, QAA, IAT, ATA, FAT, WAT, VAT, LAT, AAT, PAT, IHT, IPT, IIT, IMT, IST, ITT, IQT, IAS, IGS, IVS, ISS, ITS, IQS, INS, IAY, IAE, IAI, and AT.

* * * * *

SEQUENCE LISTING

<160> NUMBER OF SEQ ID NOS: 101

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide construct

<400> SEQUENCE: 1

Ala Ala Ala Ala Ala Ala Ala Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide construct

<400> SEQUENCE: 2

Ala Ala Ala Ala Ala Ala Ala Ala Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide construct

<400> SEQUENCE: 3

Gly Ile Ala Ala Ile Ala Ala Ala Ile
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide construct

<400> SEQUENCE: 4

Ala Ile Ala Ala Ile Ala Ala Ala Ile
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 5

Ile Ala Ala Ala Ile Ala Ala Ile Ala Ala Ala Ile
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 6

Val Ala Ala Ala Ile Ala Ala Ile Ala Ala Ala Ile

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 7

Phe Ala Ala Ala Ile Ala Ala Ile Ala Ala Ala Ile
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 8

Pro Ala Ala Ala Ile Ala Ala Ile Ala Ala Ala Ile
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 9

Ala Ala Ala Ala Ile Ala Ala Ile Ala Ala Ala Ile
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 10

Leu Ala Ala Ala Ile Ala Ala Ile Ala Ala Ala Ile
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 11

Gln Ala Ala Ala Ile Ala Ala Ile Ala Ala Ala Ile
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 12

Ile Ala Thr Ala Ile Ala Ala Ile Ala Ala Ala Ile
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 13

Ala Thr Ala Ala Ile Ala Ala Ile Ala Ala Ala Ile
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 14

Phe Ala Thr Ala Ile Ala Ala Ile Ala Ala Ala Ile
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 15

Trp Ala Thr Ala Ile Ala Ala Ile Ala Ala Ala Ile
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 16

Val Ala Thr Ala Ile Ala Ala Ile Ala Ala Ala Ile
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 17

Leu Ala Thr Ala Ile Ala Ala Ile Ala Ala Ala Ile
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 18

Ala Ala Thr Ala Ile Ala Ala Ile Ala Ala Ala Ile
1               5                   10

<210> SEQ ID NO 19

```
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 19

Pro Ala Thr Ala Ile Ala Ala Ile Ala Ala Ala Ile
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 20

Thr Ala Thr Ala Ile Ala Ala Ile Ala Ala Ala Ile
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 21

Ile His Thr Ala Ile Ala Ala Ile Ala Ala Ala Ile
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 22

Ile Pro Thr Ala Ile Ala Ala Ile Ala Ala Ala Ile
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 23

Ile Ile Thr Ala Ile Ala Ala Ile Ala Ala Ala Ile
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 24

Ile Met Thr Ala Ile Ala Ala Ile Ala Ala Ala Ile
1               5                   10

<210> SEQ ID NO 25
<211> LENGTH: 12
<212> TYPE: PRT
```

```
<213> ORGANISM: Artificial Sequence
<220> FEATURE:
<223> OTHER INFORMATION: Synthetic polypeptide construct

<400> SEQUENCE: 25

Ile Ser Thr Ala Ile Ala Ala Ile Ala Ala Ala Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 26

Ile Thr Thr Ala Ile Ala Ala Ile Ala Ala Ala Ile
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 27

Ile Gln Thr Ala Ile Ala Ala Ile Ala Ala Ala Ile
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 28

Ile Ala Ser Ala Ile Ala Ala Ile Ala Ala Ala Ile
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 29

Ile Gly Ser Ala Ile Ala Ala Ile Ala Ala Ala Ile
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 30

Ile Val Ser Ala Ile Ala Ala Ile Ala Ala Ala Ile
1               5                   10

<210> SEQ ID NO 31
<211> LENGTH: 12
<212> TYPE: PRT
<213> ORGANISM: Artificial Sequence
<220> FEATURE:
```

<223> OTHER INFORMATION: Synthetic polypeptide construct

<400> SEQUENCE: 31

Ile Ser Ser Ala Ile Ala Ala Ile Ala Ala Ala Ile
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 32

Ile Thr Ser Ala Ile Ala Ala Ile Ala Ala Ala Ile
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 33

Ile Gln Ser Ala Ile Ala Ala Ile Ala Ala Ala Ile
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 34

Ile Asn Ser Ala Ile Ala Ala Ile Ala Ala Ala Ile
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 35

Ile Ala Tyr Ala Ile Ala Ala Ile Ala Ala Ala Ile
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 36

Ile Ala Glu Ala Ile Ala Ala Ile Ala Ala Ala Ile
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide construct

```
<400> SEQUENCE: 37

Ile Ala Ile Ala Ile Ala Ala Ile Ala Ala Ala Ile
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 38

Ile Ala Thr Ala Gly Ala Ala Gly Ala Ala Ala Gly
1               5                   10

<210> SEQ ID NO 39
<211> LENGTH: 8
<212> TYPE: PRT
<213> ORGANISM: Artificial Sequence
<220> FEATURE:
<223> OTHER INFORMATION: Synthetic polypeptide construct

<400> SEQUENCE: 39

Ile Ala Thr Ala Ala Ala Ala Ala
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic polypeptide construct

<400> SEQUENCE: 40

Ile Ala Thr Ala Ala Ala Ala Ala Ala Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 41

Ile Ala Thr Ala Ala Ala Ala Ala Ala Ala Ala Ala
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 42

Ile Ala Thr Gly Ile Ala Ala Ile Ala Ala Ala Ile
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 43
```

Ile Ala Thr Ala Ile Ala Ala Ile Ala Ala Ala Ile
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 44

Glu Ala Thr Ala Ile Ala Ala Ile Ala Ala Ala Ile
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic polypeptide construct

<400> SEQUENCE: 45

Glu Ala Ala Ala Ile Ala Ala Ile Ala Ala Ala Ile
1               5                   10

<210> SEQ ID NO 46
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 46

Ala Ile Glu Glu Ile Ala Glu Ala Ile Glu Glu Ile Ala Lys Ala Ile
1               5                   10                  15

Lys Lys Ile Ala
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 47

Ala Ile Lys Lys Ile Ala Lys Ala Ile Lys Lys Ile Ala Lys Ala Ile
1               5                   10                  15

Lys Lys Ile Ala
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 48

Ala Ile Thr Thr Lys Ala Thr Ala Ile Thr Thr Glu Ala Thr Ala Ile
1               5                   10                  15

Thr Thr Ile Ala
            20

<210> SEQ ID NO 49
<211> LENGTH: 20

```
<212> TYPE: PRT
<213> ORGANISM: Artificial Sequence
<220> FEATURE:
<223> OTHER INFORMATION: Synthetic polypeptide construct

<400> SEQUENCE: 49

Ala Ile Leu Leu Lys Ala Leu Gly Ile Leu Leu Glu Ala Leu Gly Ile
1               5                   10                  15
Leu Leu Ile Ala
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 50

Ala Ile Glu Lys Ile Ala Glu Ala Ile Glu Glu Ile Ala Lys Ala Ile
1               5                   10                  15
Glu Lys Ile Ala
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 51

Ala Ile Glu Thr Ile Ala Glu Ala Ile Lys Lys Ile Ala Lys Ala Ile
1               5                   10                  15
Glu Thr Ile Ala
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 52

Ala Ile Glu Leu Ile Ala Glu Ala Ile Thr Thr Ile Ala Lys Ala Ile
1               5                   10                  15
Glu Leu Ile Ala
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 53

Ala Ile Lys Glu Ile Ala Glu Ala Glu Leu Leu Ile Ala Lys Ala Ile
1               5                   10                  15
Lys Glu Ile Ala
            20

<210> SEQ ID NO 54
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 54

Ala Ile Thr Leu Ile Ala Glu Ala Ile Lys Thr Ile Ala Lys Ala Ile
1               5                   10                  15

Thr Leu Ile Ala
        20

<210> SEQ ID NO 55
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 55

Ala Ile Leu Glu Ile Ala Glu Ala Ile Lys Leu Ile Ala Lys Ala Ile
1               5                   10                  15

Leu Glu Ile Ala
        20

<210> SEQ ID NO 56
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 56

Ala Ile Thr Glu Ile Ala Glu Ala Ile Leu Lys Ile Ala Lys Ala Ile
1               5                   10                  15

Thr Glu Ile Ala
        20

<210> SEQ ID NO 57
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 57

Ala Ile Leu Thr Ile Ala Glu Ala Ile Tyr Lys Ile Ala Lys Ala Ile
1               5                   10                  15

Leu Thr Ile Ala
        20

<210> SEQ ID NO 58
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 58

Ala Ile Glu Lys Ile Ala Thr Ala Ile Glu Glu Ile Ala Leu Ala Ile
1               5                   10                  15

Glu Lys Ile Ala
        20

<210> SEQ ID NO 59
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 59

Ala Ile Glu Thr Ile Ala Thr Ala Ile Lys Lys Ile Ala Leu Ala Ile
1               5                   10                  15

Glu Thr Ile Ala
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 60

Ala Ile Glu Leu Ile Ala Thr Ala Glu Thr Thr Ile Ala Leu Ala Ile
1               5                   10                  15

Lys Glu Ile Ala
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 61

Ala Ile Lys Glu Ile Ala Thr Ala Glu Leu Leu Ile Gly Leu Ala Ile
1               5                   10                  15

Glu Leu Ile Ala
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 62

Ala Ile Thr Leu Ile Ala Thr Ala Ile Lys Thr Ile Ala Leu Ala Glu
1               5                   10                  15

Thr Leu Ile Ala
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 63

Ala Ile Leu Glu Ile Ala Thr Ala Ile Lys Leu Ile Ala Leu Ala Glu
1               5                   10                  15

Leu Glu Ile Ala
            20

<210> SEQ ID NO 64
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 64

Ala Ile Thr Glu Ile Ala Thr Ala Ile Leu Lys Ile Ala Leu Ala Ile
1               5                   10                  15

Thr Glu Ile Ala
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 65

Ala Ile Leu Thr Glu Ala Thr Ala Ile Thr Lys Ile Ala Leu Ala Glu
1               5                   10                  15

Leu Thr Ile Ala
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 66

Ala Ile Glu Lys Ile Ala Ala Ala Ile Glu Glu Ile Ala Arg Ala Ile
1               5                   10                  15

Glu Lys Ile Ala
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 67

Ala Ile Glu Thr Ile Ala Ala Ala Ile Lys Lys Ile Ala Arg Ala Ile
1               5                   10                  15

Glu Thr Ile Ala
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 68

Ala Ile Glu Leu Ile Ala Ala Ala Glu Thr Thr Ile Ala Arg Ala Ile
1               5                   10                  15

Glu Leu Ile Ala
            20

<210> SEQ ID NO 69
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 69

Ala Ile Lys Thr Ile Ala Ala Ala Glu Leu Leu Ile Ala Arg Ala Ile
1               5                   10                  15

Lys Thr Ile Ala
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 70

Ala Ile Lys Leu Ile Ala Ala Ala Glu Thr Leu Ile Ala Arg Ala Ile
1               5                   10                  15

Lys Leu Ile Ala
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 71

Ala Ile Glu Lys Ile Ala Asn Ala Ile Glu Glu Ile Ala Cys Ala Ile
1               5                   10                  15

Glu Lys Ile Ala
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 72

Ala Ile Glu Thr Ile Ala Asn Ala Ile Lys Lys Ile Ala Cys Ala Ile
1               5                   10                  15

Glu Thr Ile Ala
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 73

Ala Ile Glu Leu Ile Ala Asn Ala Glu Thr Thr Ile Ala Cys Ala Ile
1               5                   10                  15

Lys Thr Ile Ala
            20

<210> SEQ ID NO 74
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 74

Ala Ile Lys Thr Ile Ala Asn Ala Glu Leu Leu Ile Ala Cys Ala Ile
1               5                   10                  15

Glu Leu Ile Ala
            20

<210> SEQ ID NO 75
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 75

Ala Ile Lys Leu Ile Ala Asn Ala Glu Thr Leu Ile Ala Cys Ala Ile
1               5                   10                  15

Lys Leu Ile Ala
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 76

Ala Ile Glu Lys Ile Ala Gln Ala Ile Glu Glu Ile Ala His Ala Ile
1               5                   10                  15

Glu Lys Ile Ala
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 77

Ala Ile Glu Thr Ile Ala Gln Ala Ile Lys Lys Ile Ala His Ala Ile
1               5                   10                  15

Glu Thr Ile Ala
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 78

Ala Ile Glu Leu Ile Ala Gln Ala Glu Thr Thr Ile Ala His Ala Ile
1               5                   10                  15

Glu Leu Ile Ala
            20

<210> SEQ ID NO 79
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 79

Ala Ile Lys Thr Ile Ala Gln Ala Glu Leu Leu Ile Ala His Ala Ile
1               5                   10                  15

Lys Thr Ile Ala
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 80

Ala Ile Lys Leu Ile Ala Gln Ala Glu Thr Leu Ile Ala His Ala Ile
1               5                   10                  15

Lys Leu Ile Ala
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 81

Ala Ile Glu Lys Ile Ala Ile Ala Ile Glu Glu Ile Ala Met Ala Ile
1               5                   10                  15

Glu Lys Ile Ala
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 82

Ala Ile Glu Thr Ile Ala Ile Ala Ile Lys Lys Ile Ala Met Ala Ile
1               5                   10                  15

Glu Thr Ile Ala
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 83

Ala Ile Glu Leu Ile Ala Ile Ala Glu Thr Thr Ile Gly Met Ala Ile
1               5                   10                  15

Lys Thr Ile Ala
            20

<210> SEQ ID NO 84
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 84

Ala Ile Lys Thr Ile Ala Ile Ala Glu Leu Leu Ile Gly Met Ala Ile
1               5                   10                  15

Glu Leu Ile Ala
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 85

Ala Ile Lys Leu Ile Ala Ile Ala Glu Thr Leu Ile Gly Met Ala Ile
1               5                   10                  15

Lys Leu Ile Ala
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 86

Ala Ile Glu Lys Ile Ala Phe Ala Ile Glu Glu Ile Ala Ser Ala Ile
1               5                   10                  15

Glu Lys Ile Ala
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 87

Ala Ile Glu Thr Ile Ala Phe Ala Ile Lys Lys Ile Ala Ser Ala Ile
1               5                   10                  15

Glu Thr Ile Ala
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 88

Ala Ile Glu Leu Ile Ala Phe Ala Glu Thr Thr Ile Ala Ser Ala Ile
1               5                   10                  15

Lys Leu Ile Ala
            20

<210> SEQ ID NO 89
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 89

Ala Ile Lys Thr Ile Ala Phe Ala Glu Leu Leu Ile Ala Ser Ala Ile
1               5                   10                  15
Glu Thr Ile Ala
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 90

Ala Ile Lys Leu Ile Ala Phe Ala Glu Thr Leu Ile Ala Ser Ala Ile
1               5                   10                  15
Lys Leu Ile Ala
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 91

Ala Ile Glu Lys Ile Ala Trp Ala Ile Glu Glu Ile Ala Tyr Ala Ile
1               5                   10                  15
Glu Lys Ile Ala
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 92

Ala Ile Glu Ile Ile Ala Trp Ala Ile Lys Lys Ile Ala Tyr Ala Ile
1               5                   10                  15
Glu Thr Ile Ala
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 93

Ala Ile Glu Leu Ile Ala Trp Ala Glu Thr Thr Ile Ala Tyr Ala Ile
1               5                   10                  15
Lys Leu Ile Ala
            20

<210> SEQ ID NO 94
<211> LENGTH: 20
```

```
<212> TYPE: PRT
<213> ORGANISM: Artificial Sequence
<220> FEATURE:
<223> OTHER INFORMATION: Synthetic polypeptide construct

<400> SEQUENCE: 94

Ala Ile Lys Thr Ile Ala Trp Ala Glu Leu Leu Ile Ala Tyr Ala Ile
1               5                   10                  15

Glu Thr Ile Ala
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 95

Ala Ile Lys Leu Ile Ala Trp Ala Glu Thr Leu Ile Ala Tyr Ala Ile
1               5                   10                  15

Lys Leu Ile Ala
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 96

Ala Ile Glu Lys Ile Ala Val Ala Ile Glu Glu Ile Ala Pro Ala Ile
1               5                   10                  15

Glu Lys Ile Ala
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 97

Ala Ile Glu Thr Ile Ala Val Ala Ile Lys Lys Ile Ala Pro Ala Ile
1               5                   10                  15

Glu Thr Ile Ala
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 98

Ala Ile Glu Leu Ile Ala Val Ala Glu Thr Thr Ile Ala Pro Ala Ile
1               5                   10                  15

Lys Leu Ile Ala
            20

<210> SEQ ID NO 99
<211> LENGTH: 20
```

-continued

```
<212> TYPE: PRT
<213> ORGANISM: Artificial Sequence
<220> FEATURE:
<223> OTHER INFORMATION: Synthetic polypeptide construct

<400> SEQUENCE: 99

Ala Ile Lys Thr Ile Ala Val Ala Glu Leu Leu Ile Ala Pro Ala Ile
1               5                   10                  15

Glu Thr Ile Ala
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 100

Ala Ile Lys Leu Ile Ala Val Ala Glu Thr Leu Ile Ala Pro Ala Ile
1               5                   10                  15

Lys Leu Ile Ala
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic polypeptide construct

<400> SEQUENCE: 101

Lys Ile Glu Ala Ile Glu Lys Lys Ile Glu Ala Ile Glu Lys Lys Ile
1               5                   10                  15

Glu Ala Ile Glu
            20
```